US012163871B2

(12) United States Patent
Jensen

(10) Patent No.: US 12,163,871 B2
(45) Date of Patent: Dec. 10, 2024

(54) FLUSHING DEVICE FOR A MILK SAMPLER

(71) Applicant: Smarta Industrial Pty Ltd, Cranbourne (AU)

(72) Inventor: Ashley Jensen, Cranbourne (AU)

(73) Assignee: Smarta Industrial Pty Ltd, Cranbourne (AU)

( * ) Notice: Subject to any disclaimer, the term of this patent is extended or adjusted under 35 U.S.C. 154(b) by 238 days.

(21) Appl. No.: 17/639,879

(22) PCT Filed: Sep. 2, 2020

(86) PCT No.: PCT/AU2020/000098
§ 371 (c)(1),
(2) Date: Mar. 2, 2022

(87) PCT Pub. No.: WO2021/042152
PCT Pub. Date: Mar. 11, 2021

(65) Prior Publication Data
US 2022/0291089 A1    Sep. 15, 2022

(30) Foreign Application Priority Data
Sep. 2, 2019    (AU) .............................. 2019903231

(51) Int. Cl.
| | | |
|---|---|---|
| *G01F 15/00* | (2006.01) | |
| *G01F 11/12* | (2006.01) | |
| *G01F 11/20* | (2006.01) | |
| *G01N 1/14* | (2006.01) | |
| *G01N 1/18* | (2006.01) | |
| *G01N 33/04* | (2006.01) | |
| *G01F 15/063* | (2022.01) | |
| *G01F 15/12* | (2006.01) | |
| *G01N 1/10* | (2006.01) | |

(52) U.S. Cl.
CPC ............. *G01N 1/14* (2013.01); *G01F 11/125* (2013.01); *G01N 1/18* (2013.01); *G01N 33/04* (2013.01); *G01F 15/063* (2013.01); *G01F 15/12* (2013.01); *G01N 2001/1081* (2013.01); *G01N 2001/185* (2013.01)

(58) Field of Classification Search
CPC .... G01N 1/14; G01N 1/18; G01N 2001/1081; G01N 2001/185; G01N 33/04; G01F 11/125; G01F 15/001; G01F 15/022; G01F 15/063; G01F 15/01; A01J 5/045
See application file for complete search history.

(56) References Cited

U.S. PATENT DOCUMENTS 3,554,674 A    1/1971   Huret
3,965,750 A *  6/1976   Johnson .................... G01N 1/12
                                                     73/864.51
(Continued)

FOREIGN PATENT DOCUMENTS

JP        2007531869 A  *  11/2007

*Primary Examiner* — Andre J Allen
(74) *Attorney, Agent, or Firm* — Chernoff, Vilhauer, McClung & Stenzel, LLP

(57) ABSTRACT

A sampler including an inlet, an outlet and a flushing device. The sampler adapted such that a sample fluid flows from the inlet, out the outlet and into sample containers. The flushing device is adapted to flush a pressurised pressurized flushing fluid past all surfaces of the sampler which are adapted to contact the sample fluid.

16 Claims, 16 Drawing Sheets

(56) References Cited

U.S. PATENT DOCUMENTS

| | | | | |
|---|---|---|---|---|
| 4,009,617 | A | * | 3/1977 | Johnson .................... G01N 1/14 |
| | | | | 417/520 |
| 4,147,062 | A | * | 4/1979 | Jaeger .................. G01N 1/2035 |
| | | | | 73/863.83 |
| 4,269,064 | A | * | 5/1981 | Johnson ............... G01N 1/2035 |
| | | | | 73/863.82 |
| 2001/0055533 | A1 | | 12/2001 | Lang et al. |
| 2009/0242076 | A1 | | 10/2009 | Janeau et al. |
| 2012/0160174 | A1 | * | 6/2012 | Gudmundsson ........ A01J 5/045 |
| | | | | 119/14.02 |
| 2016/0025601 | A1 | * | 1/2016 | Newbold ............. G01N 1/2226 |
| | | | | 73/864.81 |
| 2019/0082659 | A1 | * | 3/2019 | Mottram ............... A01J 5/0135 |

\* cited by examiner

FLUSHING DEVICE FOR A MILK SAMPLER

FIELD OF INVENTION

This invention relates to a sampler. More particularly, this invention relates to a sampler with a flushing device. More particularly, this invention relates to a sampler with a cleaning device capable of a flushing or purging action, component or step. Most particularly, this invention relates to a milk sampler.

BACKGROUND ART

The following references to and descriptions of prior proposals or products are not intended to be, and are not to be construed as, statements or admissions of common general knowledge in the art. In particular, the following prior art discussion should not be assumed to relate to what is commonly or well known by the person skilled in the art, but to assist in the inventive process undertaken by the inventor(s) and in the understanding of the invention.

Milk samplers have been described in which small samples of milk product are obtained. However, milk residue may remain in a tube or pipe of a prior art milk sampler from previous sample runs. This can present a contamination risk and potentially affect the accuracy of any measurements. In the context of commercial dairy production, such spoilage or measurement errors can have significant and dire affects.

An object of the present invention is to ameliorate one or more of the aforementioned disadvantages of the prior art or to at least provide a useful alternative thereto.

STATEMENT OF INVENTION

The invention according to one or more aspects is as defined in the independent claims. Some optional and/or preferred features of the invention are defined in the dependent claims.

Accordingly, in one aspect of the invention there is provided:

A sampler including an inlet, an outlet, a sample dispenser and a flushing device, the sampler adapted to receive a sample fluid through the inlet, and to dispense the sample fluid through the outlet into sample containers, wherein, the flushing device is adapted to flush a pressurised flushing fluid past all surfaces of the sample dispenser which are adapted to contact the sample fluid.

In another aspect of the same invention, there is provided a sampler including:
- an inlet adapted to receive a sample fluid;
- a plurality of contact surfaces forming part of at least one flexible conduit adapted to come into contact with the sample fluid;
- a sample dispenser adapted to dispense the sample fluid from an outlet into one or more sample containers; and
- and a flushing device for cleaning the sampler, wherein the flushing device is adapted on actuation to:
- move the flexible conveyance from a compressed state to a non-compressed state; and deliver a pressurised flushing fluid passed all of the contact surfaces.

Sample Dispenser

The sample dispenser may further include a reciprocating pump such as a piston or diaphragm pump and/or a rotary pump such as a centrifugal pump. Preferably, the sample dispenser includes at least one peristaltic pump.

The sampler may further include a controller. The pump may be controlled by the controller. The pump, under the control of the controller, may be adapted to cause the sample fluid to move through the inlet and outlet for a specified amount of time to deliver a specified amount of fluid through the outlet and into the sample containers.

Inlet

The sampler may be adapted such that sample fluid flows from a sample fluid vessel into the inlet in a dispensing process. The sample fluid vessel may be any container used to store the sample fluid. The sample fluid vessel may include a stationary container or tank. The sampler may be adapted to be mounted to sample fluid vessels at a factory, silo and/or other stationary locations. The factory may be adapted to receive sample fluid from tankers. The sampler may include multiple interchangeable mounting surfaces each adapted to be mounted to different sample fluid vessels. The sampler may be adapted to take samples of sample fluid flowing through a pipe. Advantageously, the sampler may take samples of sample fluid flowing through a pipe. This may result in a sample more representative of all the sample fluid in the sample fluid vessel. Preferably, the samples are taken in the dispensing process. Preferably, the sample fluid vessel includes a tank on the tanker. The tanker may include a ship, road vehicle or aircraft. Preferably, the tanker is a road vehicle. Preferably, the tanker is a truck or heavy vehicle. The sample fluid vessel may be adapted to be mounted on a tanker or semi-trailer.

The inlet may include at least one inlet pipe continuous with, or connected to an inlet port. Preferably, the inlet includes two inlet pipes. The inlet pipe may be welded, bolted or otherwise attached to the sample fluid vessel. The inlet may be welded onto the outside of the sample fluid vessel and adapted to receive sample fluid through a hole in the sample fluid vessel. The hole in the sample fluid vessel may be substantially flush with an opening or end surface of the inlet pipe. Preferably, the inlet pipe extends through a hole in the sample fluid vessel. Most preferably, the inlet pipe extends into a cavity of the sample fluid vessel. In use, the opening of the inlet pipe is preferably adapted to be immersed in the sample fluid. The sample fluid vessel may include pipes or other hollow objects with cavities continuous and in fluid communication with a cavity of a main tank of the sample fluid vessel. Preferably, the inlet pipe extends into a cavity of a pipe of the sample fluid vessel. Preferably, an end of the inlet pipe which extends into the sample fluid vessel includes a rounded or radiused outer edge. Preferably, the inlet pipe is a spigot adapted to connect to a flexible conduit in the form of a flexible tube. Preferably, the inlet pipe includes a barbed end adapted to receive the flexible tube. Preferably, the flexible tube is adapted to stretch and/or slide over the barbed end therefore attaching itself to the barbed end. The barbed end may include multiple barbs. Preferably, the barbed end includes only a single barb.

The sampler may include bolts, clamps, gaskets, seals and/or interlocking components adapted to attach and/or seal the sampler to the sample fluid vessel. Preferably, the sampler includes at least one mounting surface that is adapted to be mounted to the sample fluid vessel. Preferably, the mounting surface is adapted to be welded to the sample fluid vessel. Most preferably, the mounting surface is welded to the pipe of the sample fluid vessel. The mounting surface may be any shape. Preferably, the mounting surface follows the contours or shape of the sample fluid vessel where the sample dispenser is mounted. Preferably, the mounting surface is in the shape of a partial cylinder or is part-cylindrical.

The inlet pipe may be formed, in part, from a hole through at least one component of the sampler. The inlet pipe may include at least one substantially rigid or flexible pipe. The inlet pipe may include a funnel or tapered inlet. The inlet pipe may include at least one manual or automatic valve. The automatic valve may include an air, electronic or hydraulic actuated valve. Preferably, the inlet pipe does not include a valve. Preferably, the pump stops and allows flow of sample fluid through the sampler.

The inlet may be integrally formed with and/or be continuous with other components of the sampler. The inlet may include a removeable insert. Preferably, the inlet is a removeable insert mountable to other components of the sampler. Preferably, the inlet is removable from and mountable to other components of the sampler.

Outlet

There may be multiple outlets, but in any case, there is at least one outlet. The outlet may include at least one outlet port. The outlet may include at least one outlet pipe. Preferably, the outlet includes two or more outlet pipes, including a first and a second inlet pipe. Preferably, the first inlet pipe is adapted to receive a particular first sample of sample fluid, and the sampler is adapted to feed the first sample, for example by the conveyance, to a first outlet pipe. Similarly, preferably the second inlet pipe is adapted to feed sample fluid, for example by the conveyance, to a second outlet pipe during a dispensing process. The outlet pipe may be formed at at least one outlet port or hole that extends through a part, a flexible tube, an insert, a solid pipe and/or other features. The outlet pipe may include a hollow syringe-type needle or a narrow pipe. The narrow pipe may be tapered from a wide base down to a narrower free end at an outlet nozzle. Preferably, the outlet pipe includes a needle. Preferably, each of the first and second outlet pipes includes a needle. Preferably, the outlet is adapted such that sample fluid flows out of the first and/or second needle into respective first and/or second sample containers during a dispensing process.

The outlet may be integrally formed with and/or be continuous with other components of the sampler. Preferably, the outlet is a removable insert. Preferably, the outlet is removeable from and mountable to other components of the sampler. The outlet may be adapted to be screwed into the main body. The outlet may be adapted to be press fit or otherwise attached to the main body. Preferably, the outlet is adapted to be inserted into the outlet hole of the main body and locked in place with multiple shafts, and in any case, at least one moveable shaft. Preferably, a spring applies axial force to the moveable shaft to keep it in a locked position. Preferably, the moveable shaft is adapted to extend out of the main body and is adapted to be pressed and moved axially to unlock the outlet. Preferably, longitudinal axis of the moveable shaft is adapted to be perpendicular to longitudinal axis of the outlet. Preferably, at least a portion of the moveable shaft is adapted to be removably inserted into a smaller diameter feature in the outlet in the locked position such that the outlet cannot move axially.

Peristaltic Pump

The flushing device may include a toggle mechanism. The flushing device may be adapted to apply tension to the conveyance during the sampling phase. The flushing device may be adapted to release the tension on the conveyance during the purging or flushing phase. The flexible conveyance may include one or more compartments, containers, chambers, pipes or tubes adapted to come into contact with the sample fluid. Preferably, the flexible conveyance includes at least one flexible tube. The contact surfaces may be the internal wall surfaces of the conveyance. The contact surfaces may be the internal wall surfaces of the flexible tube.

Preferably, the peristaltic pump includes one or more tubes. Preferably, the peristaltic tubes are cylindrical (or substantially round or circular in cross-section) in an uncompressed state. Preferably, the peristaltic tubes are flexible tubes. Preferably, the flexible tubes are detachable and replaceable. The peristaltic pump may include a rotating member. The rotating member may be any part of the peristaltic pump which rotates. A length of the flexible tubes which is adapted to contact the rotating member may be longer, the same or shorter than a length of the flexible tubes which does not contact the rotating member. The length of the flexible tubes which is adapted to contact the rotating member may be at least 20% of a full length of the flexible tubes Preferably, the length of the flexible tubes which is adapted to contact the rotating member is at least 30% of a full length of the flexible tubes. The flexible tubes may be adapted to be replaced on a regular basis. The flexible tubes may be adapted to be replaced after any period. The flexible tubes may be adapted to be replaced between every 1 to 10 days. Preferably, the flexible tubes are adapted to be replaced between every 2 to 4 days. Preferably, the needles are located at a first end of the outlet pipe. Preferably, the sampler is adapted such that sample fluid flows out of the needles in the dispensing process.

The flexible tubes may be adapted to be attached to the outlet and/or inlet by the ends of the flexible tube being located on barbed pipes of the inlet and/or outlet and secured with a clamp/clip such as a worm clamp/hose clamp. The flexible tubes may be welded onto the outlet and/or inlet. Preferably, the flexible tubes are adapted to be press fit onto the outlet and/or inlet. Preferably, the flexible tubes are adapted to be press fit over the barbed pipes inlet and/or outlet pipes. The barbed pipes may include circumferential barbs, bumps and/or grooves on an outer surface of the barbed pipes of the inlet and/or outlet. Preferably, each of the barbed pipes only has a single circumferential barb on the outer surface. Preferably, the circumferential barbs are sized to adequately secure the flexible tube onto the barbed pipes with a press fit connection. Preferably, the inlet includes barbed pipes adapted to receive first ends of the flexible tubes and the outlet also includes barbed pipes adapted to receive second ends of the flexible tubes.

Each of the two flexible tubes may individually form part of their own peristaltic pump. Preferably, the peristaltic pump includes both flexible tubes. The peristaltic pump may include an electric motor, hydraulic motor, pneumatic motor and/or other motor. Preferably, the peristaltic pump includes an electric motor. The electric motor may be a motor which is adapted to rotate the output shaft of the electric motor to a certain angle to an accuracy of, for example, +/−10 degrees of rotation. Preferably, the electric motor is a stepper motor.

Preferably, the rotating member includes peripheral surfaces. The rotating member may comprise a rotatable axle. The rotating member may comprise a plurality of longitudinally parallel beams or rods. The beams or rods may be radially equally-spaced from the rotational axis of the rotating member. The beams may be supported by one or more arms. The arms may include the peripheral surfaces. The arms may be in the form of spokes that radially extend from the axle of the rotating member.

The peripheral surfaces may include raised portions of a substantially cylindrical rotating member. Preferably, the peripheral surfaces are curved surfaces. Preferably, the peripheral surfaces are cylindrical rods. Preferably, the cylindrical rods are attached at either end to end plates of the rotating member. Preferably, the cylindrical rods rotate relative to the end plates. Preferably, the cylindrical rods are mounted to bearings and the bearings mounted to the end plates. Preferably, the end plates are attached to or form part of the axle of the rotating member. Preferably, the protruding peripheral surfaces contact a first side of the flexible tubes.

A location of a longitudinal axis of the rotating member may be moveable to apply pressure to and release pressure from the flexible tubes. Preferably, the flushing device includes a tensioning mechanism. The tensioning mechanism is preferably adapted to be selectively toggled between a tensioning state or position in the sampling mode, and a non-tensioned state or position in the flushing mode. The tensioning mechanism may include at least one clamp. The clamp may be movable to apply pressure to and/or release pressure from a second side of the flexible tubes.

Preferably, the first and second sides of the flexible tubes are radially opposite sides of the flexible tubes. Preferably, the clamp includes two arms with a first arm adapted to contact the flexible tube attached to the first inlet pipe and the first outlet pipe and a second arm adapted to contact the flexible tube attached to the second inlet pipe and the second outlet pipe. Preferably, a contact surface of the clamp, which contacts the flexible tubes, is curved. Most preferably, the contact surface of the clamp is cylindrical or is in the form of a portion of a cylinder.

Preferably, the peristaltic pump is adapted such that the flexible tubes may be compressed between the peripheral surfaces of the rotating member and the contact surfaces of the clamp. The clamp may be adapted to pivot and/or move linearly to apply pressure to and release pressure from the flexible tubes. Preferably, the first and second arms of the clamp are fixed such that they move together. Preferably, the clamp is adapted to pivot about a hinge and/or axle. The movement of the clamp may be actuated manually by a user and/or automatically by a first actuation device. The first actuation device may include a solenoid, electric motor such as a stepper motor, a pneumatic piston and/or another actuation device. Preferably, the sampler includes a pneumatically actuated piston which is adapted lock and release the clamp. Preferably, the movement of the clamp is adapted to be actuated manually by a user.

Flushing Device

The flushing device may include at least one compressor, pump, heater, pipe, tube, valve, container, shuttle valve and other features. The flushing device may produce and use steam to flush all surfaces of the sampler which contact the sample fluid. Preferably, the flushing device includes a pressurized air source. Preferably, the pressurized air source is an air compressor. Preferably, the air compressor is adapted to provide high pressure air to valves. Preferably, the flushing device includes at least one of the valves. Preferably, the valves are arranged in parallel such that air may pass through any of the valves individually without passing through any other valves. Each valve may be manually actuated and/or actuated with an actuation device. The actuation device may form part of the valve. The actuation device may include an electric motor such as a stepper motor, solenoid, pneumatic piston or other actuator.

Preferably, each valve is actuated by a solenoid. Preferably, a fourth valve of the valves is adapted to feed pressurized air through a tube and out a flushing port adapted to be connected to the outlet. Preferably, the flushing device includes two flushing ports, one adapted to flush cleaning substance through the first outlet pipe and inlet pipe and the other adapted to flush cleaning substance through the second outlet pipe and inlet pipe. Preferably, the flushing ports are moveable to be located out of alignment with the needles of the outlet pipes and to be positioned over the needles of the outlet pipes.

Preferably, the flushing ports are adapted to be positioned such that a cleaning substance coming out of the flushing ports flushes around outer surfaces of the needles of the outlet pipes and flushes the inner surfaces the outlet and inlet. Therefore, preferably, the flushing port is adapted to be positioned close to an end of the needles of the outlet pipes but not in contact with the needles of the outlet pipes. The flushing port may be adapted to create a seal with the needles of the outlet pipes. Preferably, the container of the flushing device is adapted to be pressurized. Preferably, the container is connected to the pressurized air source with a bottle pressure tube. The container may be in the form of a pressurized bottle. Preferably, the container is adapted to contain part or all of the cleaning substance. The container may include a piston separating the pressurized air from the cleaning substance. Preferably, the container includes a needle or tube extending into the container to a base of the container. The needle or tube may be connected to or be in fluid communication with the fourth valve which is in fluid communication with the flushing ports. The flushing device may include a one-way valve between the container and the fourth valve.

Preferably the needle or tube is connected to a shuttle valve with a first shuttle valve tube and the shuttle valve is connected to the fourth valve with a tube. Preferably the container is adapted such that the cleaning substance is forced through the needle or tube, through the fourth valve and out the flushing port. Preferably, the shuttle valve is also directly connected to the pressurized air source with a second shuttle valve tube such that the shuttle valve combines cleaning substance from the container and pressurized air from the pressurized air source forming a pressurized flushing fluid and sends the pressurized flushing fluid through the fourth valve and out the flushing port. The shuttle valve may be adapted to be actuated to selectively allow pressurized air and/or cleaning substance through the shuttle valve. The shuttle valve may be adapted to be actuated manually or automatically with the controller. Preferably, the shuttle valve is adapted to be actuated automatically with the controller. Therefore, preferably, the sample dispenser is adapted to allow pressurized flushing fluid to flow out the flushing port, into the outlet, around the needles of the outlet pipes, through the flexible tubes, out the inlet and into the sample fluid vessel in a flushing process. The valves may include two flushing valves to control flow of the pressurized flushing fluid. A first flushing valve of the two flushing valves may control flow of the cleaning substance from the container and a second flushing valve of the two flushing valves may control flow of the pressurized air forming part of the pressurized flushing fluid. Therefore, using the two flushing valves or the shuttle valve, the flushing device may be adapted to selectively flush pressurized air and/or cleaning substance through the surfaces of the sampler which contact the sample fluid.

Preferably, the pressurized flushing fluid is air and/or cleaning substance. Preferably, the sampler is adapted such that the air and/or cleaning substance flows through the outlet and out the inlet into the sample fluid vessel therefore flushing all surfaces of the sampler which the sample fluid contacts in the flushing process.

The pressurized flushing fluid may include air, alcohol, water, steam, disinfectants or other fluids. The cleaning substance may include alcohol, water, distilled water, disinfectants and other cleaning substances. Preferably, the cleaning substance includes alcohol and distilled water. Most preferably, the cleaning substance includes between 50% and 75% alcohol and between 25% and 50% distilled water.

Sample Holder

The sampler may further include a sample holder. The sample holder may be adapted to receive the sample containers for the dispensing process. The sample holder may include claws sized to receive a circumferential lip on the sample containers. The sample holder may include other features to hold the sample containers. Preferably, the sample holder includes a block with substantially cylindrical holes adapted to receive the sample containers.

Preferably, the block further includes the flushing ports. Preferably, the block is moveable to align either the cylindrical holes of the block directly under the needles of the outlet pipes or the flushing ports directly under the needles of the outlet pipes. The block may include multiple blocks individually actuated. Preferably, the block includes a single block. The block may be actuated by at least one solenoid, pneumatic motor, pneumatic piston, electric motor and/or other actuating devices. Preferably, the block is actuated with pneumatic pistons. The block may be supported by at least one pivot/hinge, rail, surface, arm and/or other supports. Preferably, the block is supported by two rails. The rails may be in the form of a U, V, semicircle or other shapes. Preferably, the rails are in a U-shape.

The sample holder may include a cooling device adapted to cool the sample holder. The cooling device may be adapted to cool the sample containers. The cooling system may include circulating a fluid between the sample holder and a cooler object or fluid. The cooler object or fluid may include the sample fluid vessel, sample fluid in the sample fluid vessel, a radiator/heatsink or other surfaces/fluids. The heatsink may be adapted to be located outside or inside the sample fluid vessel. Preferably, the cooling system circulates a cooling fluid between the sample holder and an outer surface of the sample fluid vessel. The cooling system may include other cooling devices such as an air conditioning system including at least one compressor, expansion valve and radiator. The cooling devices may include at least one Peltier device. The Peltier device may include placing Peltier modules between the sample holder and a heatsink. The heat sink may be positioned such that fluid flows past the heat sink. Such as inside the sample fluid vessel or adapted to be in an air stream when the road vehicle is moving. The block may include insulation such as air gaps adapted to keep the sample holder and/or the sample containers cool.

Controller

Preferably, the sample dispenser further includes the controller. Preferably, the controller controls all the valves and motors in the sample dispenser. Preferably, the controller controls the pump. Preferably, the controller controls the peristaltic pump. The controller may control the first actuation device to release the clamp. Preferably, the controller controls the valves of the flushing device. Preferably, the controller controls the solenoids which actuate the valves. Preferably, the controller controls the actuation of the block/sample holder.

The controller may include at least one display, touch screen, computer processing unit (CPU), relay, button, switch, wireless communication module, radio-frequency identification (RFID) reader and/or writer, indicator light, limit sensors and/or other sensors, and other electronic components. The wireless communication module may include at least one Wi-Fi module, global system for mobile (GSM) module, infra-red transmitter/receiver, clock and global positioning system (GPS). The controller may include a portable remote control to send controls and/or data to the rest of the controller. Preferably, the controller includes a CPU, buttons/switches and two RFID reader writers. Preferably, the RFID reader writers are located in the sample holders beside where the sample holder is adapted to receive the sample containers.

Preferably, the controller is adapted to record the global location and time where/when a dispensing process took place. Preferably, the sample containers include RFID tags which communicate with RFID devices (RFID reader writers) near each of the sample holders.

Preferably, the RFID devices individually write to the RFID tags on each of the sample containers the time and location that the dispensing process took place when those sample containers were in the sample holders. Preferably, there is one RFID device next to each of the sample holders. The controller may be adapted to connect send/receive information from/to a website and/or application on a user's electronic mobile device. The controller may be adapted such that the user can view data from the controller and/or send controls to the controller to, for example, start the dispensing and/or flushing process.

Preferably, the controller controls actuation of each component in the dispensing process. Preferably, the sample containers are adapted to be placed in the sample holders by a user. Preferably, then the following actions are all automatic in response to an input by the user into the controller such as pressing a button. Preferably, the dispensing process includes actuating the block to align holes of the block directly under the needles of the outlet pipes which is the dispensing position if it is not already in that position. Preferably, then actuating the peristaltic pump to rotate for a specified time and therefore output a specified amount of sample fluid from the needles of the outlet pipes into the sample containers. Then the dispensing process may include actuating the block to align the flushing ports with the needles of the outlet pipes such that the flushing ports cover the needles of the outlet pipes. Preferably, if the sample holder is in the dispensing position, the sample holder is automatically moved so that the block is positioned with the flushing ports covering the needles of the outlet pipes when the road vehicle is moving.

Preferably, the flushing process is done in between dispensing processes. Preferably, the flushing process is done soon after the dispensing process. Preferably, the time between a dispensing process and the flushing process done after is shorter than the time between a flushing process and the dispensing process done after. The time between a dispensing process and the flushing process done after may be less than 1 minute. The time between a dispensing process and the flushing process done after may be less than 30 seconds. Preferably, the flushing process first includes lifting the clamp off the two flexible tubes of the outlet pipes manually or automatically through the controller. Preferably, the flushing process then includes pressing a button on the controller or otherwise activating the controller to carry out the rest of the flushing process. Preferably, the flushing process includes moving the block to align the flushing ports with the needles of the outlet pipes. Preferably, the flushing process then includes activating valves which control flow of the pressurized flushing fluid. The first and/or second flushing valve may be activated in the flushing process. The first and/or second flushing valves may be activated multiple times in the flushing process. For example, the second flushing valve may allow a continuous stream of pressurized air through the sampler while the first flushing valve pulses sending bursts of cleaning substance through the sampler. Preferably, this concludes the flushing process.

Sensors

The controller may further include at least one pressure sensor, sample fluid temperature sensor and ambient temperature sensor. The pressure sensor may include multiple pressure sensors. The pressure sensor may be located inside the sample fluid vessel. The pressure sensor may be located in at least one suspension airbag of the road vehicle supporting the sample fluid vessel. The pressure sensor may be located in at least one suspension piston. The pressure sensor may include a piezoresistive strain gauge, capacitive sensor, electromagnetic sensor, piezoelectric sensor, strain-gauge sensor, optical sensor, potentiometric sensor, force balancing sensor or other pressure sensor. The pressure sensor may further include a distance sensor. The distance sensor may measure the distance between wheel axles of the road vehicle and the sample fluid vessel of at least one position on the road vehicle. The distance sensor may measure the depth of sample fluid in at least one location in the sample fluid vessel. The distance sensor may measure the distance between the distance sensor and a surface of the sample fluid in the sample fluid vessel. The distance sensor may include an infrared sensor, ultrasonic sensor, capacitive sensor or other distance sensors. The controller may be adapted to calculate the pressure from the distance measured from the distance sensor. The pressure sensor may be located in at least one suspension airbag of the road vehicle supporting the sample fluid vessel of the road vehicle. Preferably, at least part of the pressure sensor is located inside the sample fluid vessel.

Preferably, the sample fluid temperature sensor is adapted to measure the temperature of the sample fluid inside the sample fluid vessel and/or the pipe of the sample fluid vessel. Preferably, the ambient temperature sensor is adapted to measure the temperature of air surrounding the sampler. The ambient temperature sensor may be adapted to be mounted anywhere on the tanker. Preferably, the ambient temperature sensor is adapted to be mounted on the sampler. Most preferably, the ambient temperature sensor is adapted to be mounted near the flexible tubes. The sample fluid temperature sensor and/or ambient temperature sensor may include multiple temperature sensors. The sample fluid temperature sensor and ambient temperature sensor may include any type of temperature sensor. The sample fluid temperature sensor and ambient temperature sensor may include thermistors, thermocouples and other temperature sensors.

The controller may be adapted to adjust how long the peristaltic pump rotates in a dispensing process based on the ambient temperature, sample fluid temperature and/or pressure measured by the ambient temperature sensor, sample fluid temperature sensor and/or pressure sensor respectively. Preferably, the controller is adapted to adjust how long the peristaltic pump rotates in a dispensing process based on the temperature and pressure measured by the pressure sensor, ambient temperature sensor and sample fluid temperature sensor at the time of dispensing. The time of dispensing may include within 1 minute, 30 minutes, 1 hour or within other periods of time of the exact time of the dispensing process. For example, a single revolution of the rotating member of the peristaltic pump when the sample fluid temperature is 2 degrees may dispense 50 ml and when the sample fluid temperature is 5 degrees may dispense 55 ml. Therefore, the controller may be adapted to rotate the rotating member 1.1 revolutions when the sample fluid temperature is 2 degrees and 1 revolutions when the sample fluid temperature is 5 degrees in order to dispense the same amount of sample fluid at each sample fluid temperature.

The controller may be adapted to calibrate the distance sensor and/or pressure sensor by determining the distance/pressure reading from the distance/pressure sensor when the tank has a certain amount of sample fluid in it, such as when it is empty and full. The controller and/or external computer may be adapted to calculate or estimate the amount of sample fluid in the sample fluid vessel from the distance and/or pressure measured from the distance/pressure sensor.

The controller may be adapted such that the user can view how much sample fluid is in the sample fluid vessel on the display, a portable display, on the users electronic mobile device and/or on a website. The controller may be adapted to send alerts to the user such as an alert when the sample fluid vessel is full and/or empty of sample fluid. The controller may be integrated with or communicate with a device (navigation device) which the user uses to navigate. The controller may be adapted to alert the user and/or temporarily lock the user out if the road vehicle starts a new route when the tanker is not empty. The controller may be adapted to alert the user and/or temporarily lock the user out if the road vehicle ends a route. The controller may be adapted to detect when the user starts a new route and/or ends a route by detecting the user entering a destination on the navigation device and/or as detected from a change in location detected by the GPS. The controller may be adapted to alert the user and/or temporarily lock the user out when the user starts a cleaning in place (CIP) of the sample fluid vessel when the sample fluid vessel is not empty. The controller may be adapted to alert the user and/or temporarily lock the user out when the user stops CIP when the tanker is not empty.

CIP may include a CIP system external to the road vehicle. CIP may include a CIP system attached to the road vehicle. Preferably CIP includes a CIP system attached to the road vehicle. The CIP system external to the road vehicle or attached to the road vehicle (CIP systems) may include pipes adapted to connect or connected to the sample fluid vessel to deliver a cleaning fluid to the sample fluid vessel. The CIP systems may include nozzles inside or adapted to be placed inside the sample fluid vessel adapted to spray internal surfaces of the sample fluid vessel. The CIP systems may be automatically controlled with the controller. The CIP systems may include a CIP controller which communicates with the controller. Preferably, the CIP systems include a pump and the pumps on/off status is detected by the controller. Preferably, the controller switches on or turns off the pump. Locking the user out may include the display displaying a lock screen and disabling input to the controller. Locking the user out may include displaying a lock screen on a navigation device display and/or disabling input to the navigation device. Locking the user out may include temporarily disabling at least one input to the controller such as buttons or a touch screen. Locking out the user may include turning the pump of the CIP systems off or turning the pump of the CIP systems on. Advantageously, locking out the user may prevent cross contamination of sample fluid with cleaning fluid.

BRIEF DESCRIPTION OF THE DRAWINGS

The invention may be better understood from the following non-limiting description of preferred embodiments, in which.

DETAILED DESCRIPTION OF THE DRAWINGS

Figure 1:
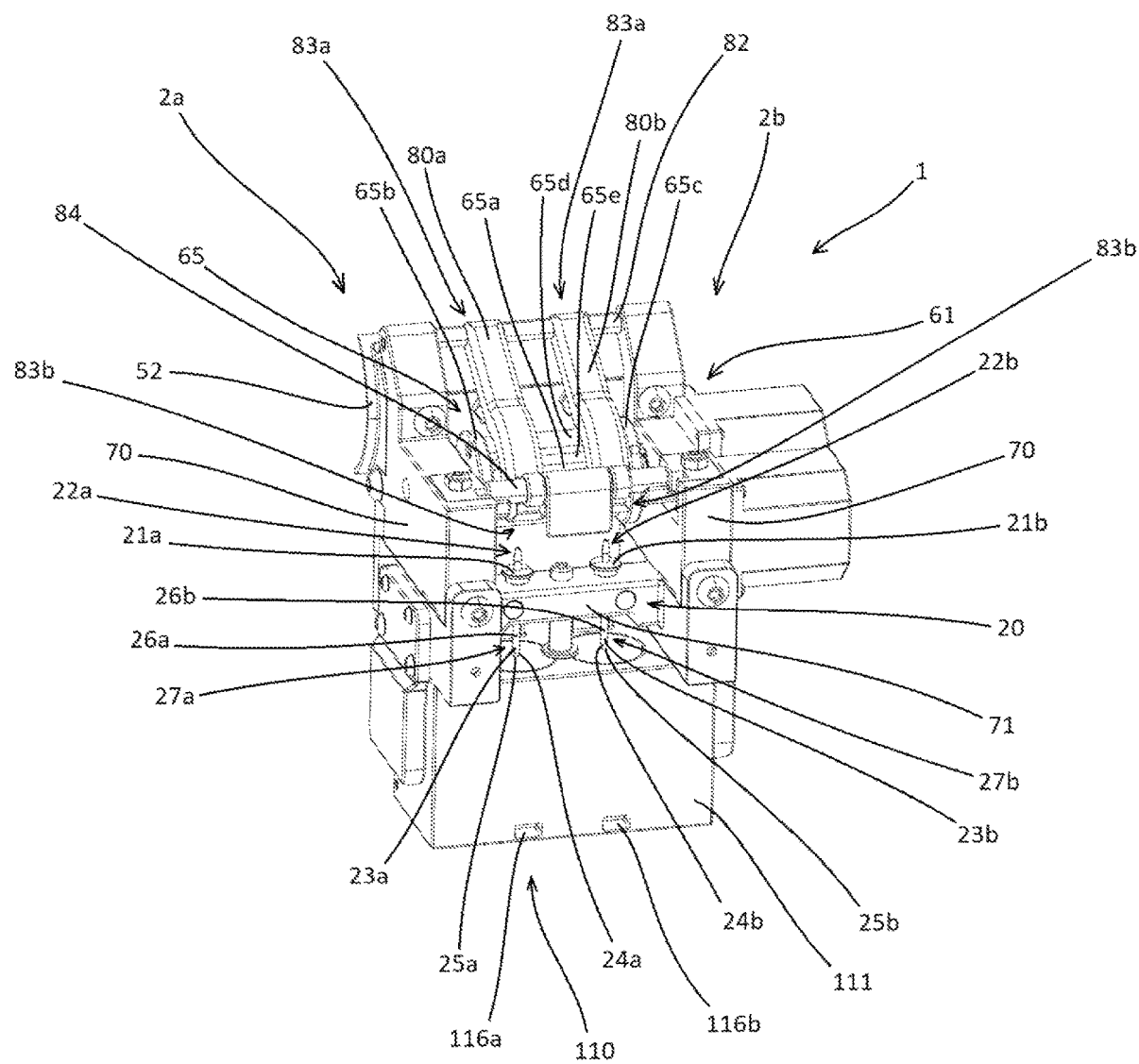
FIG. 1 is a front perspective view of a sampler without a flushing device or a controller.
Figure 1A:
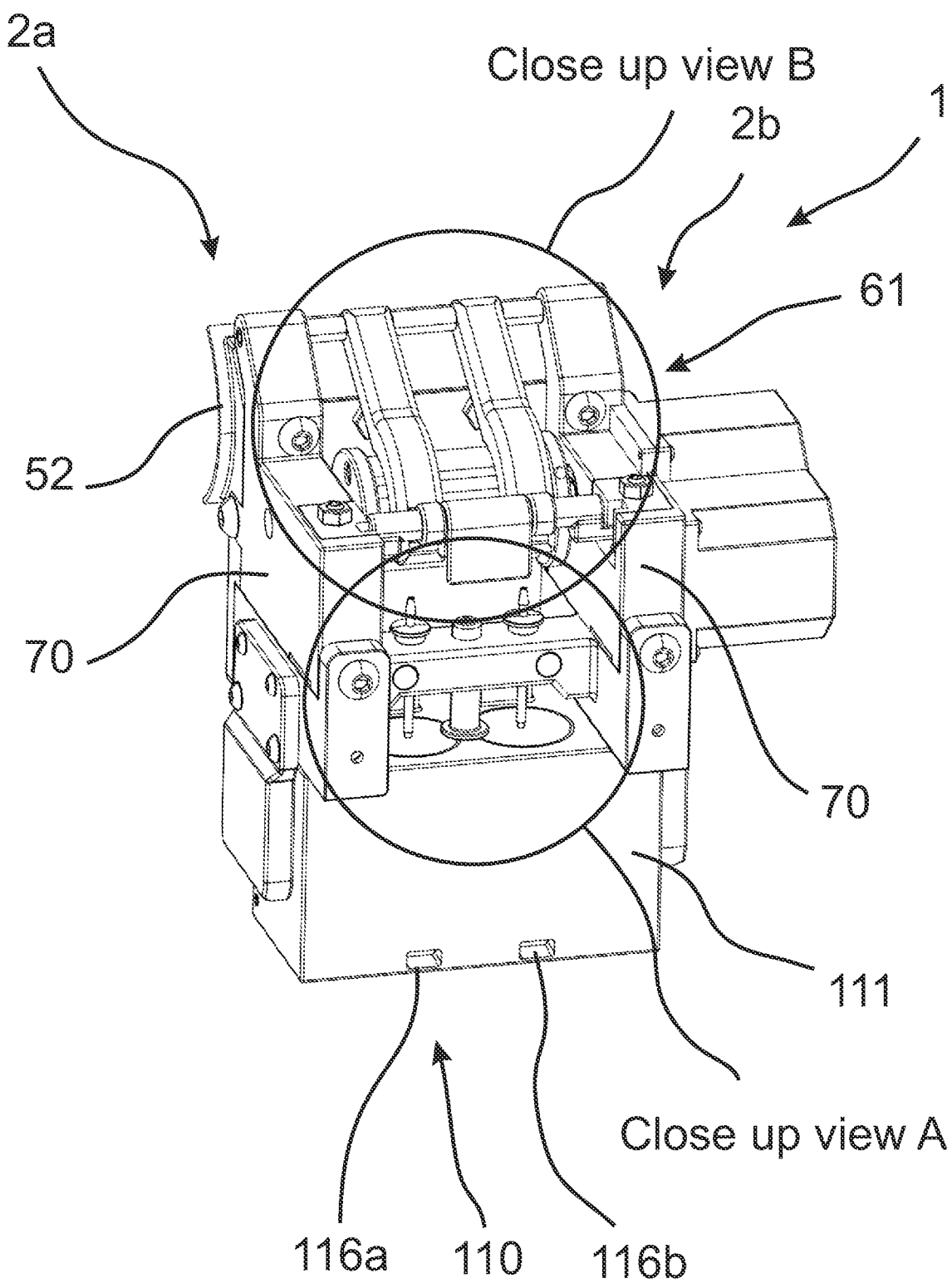
Figure 1B:
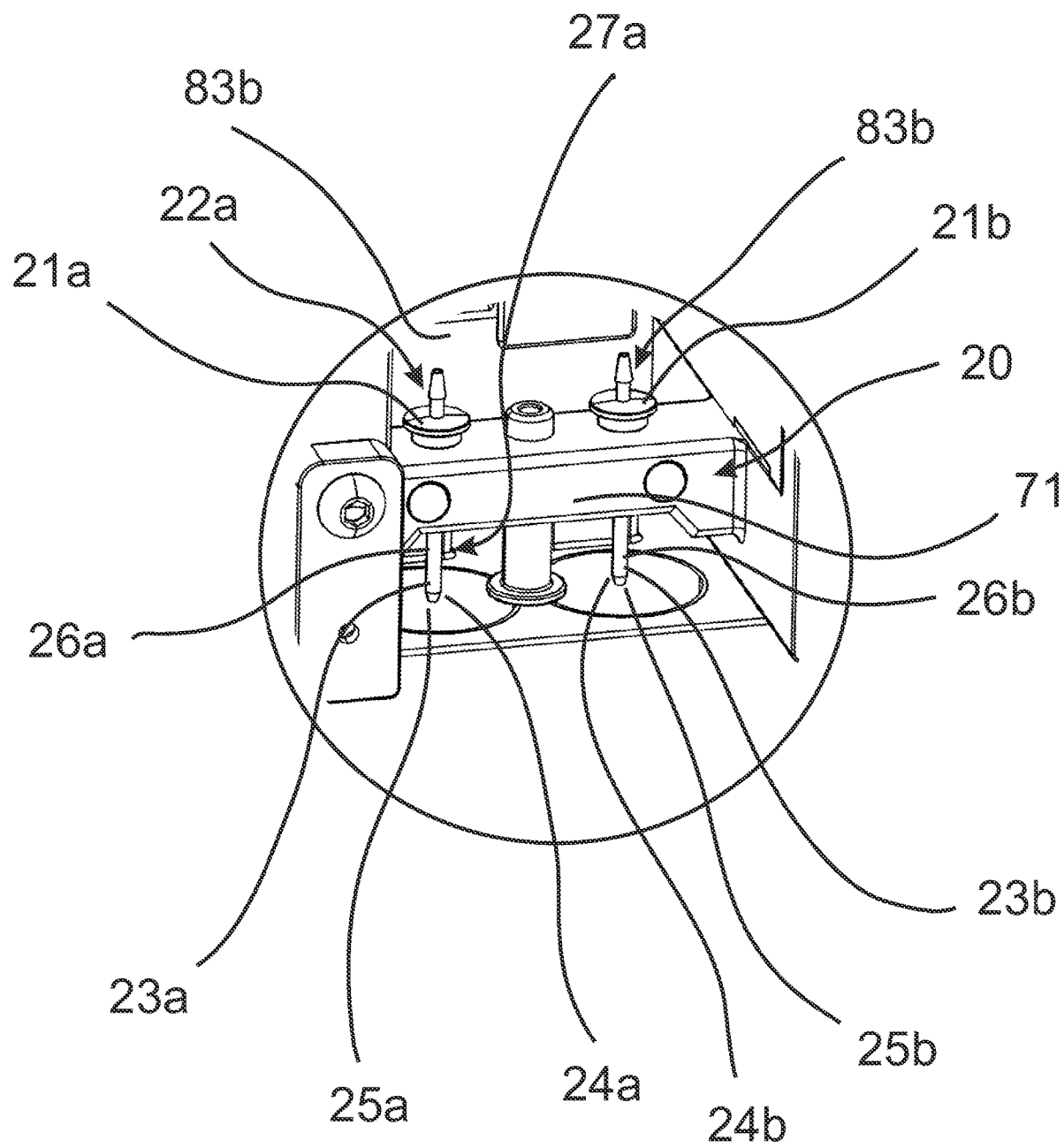
Figure 2:
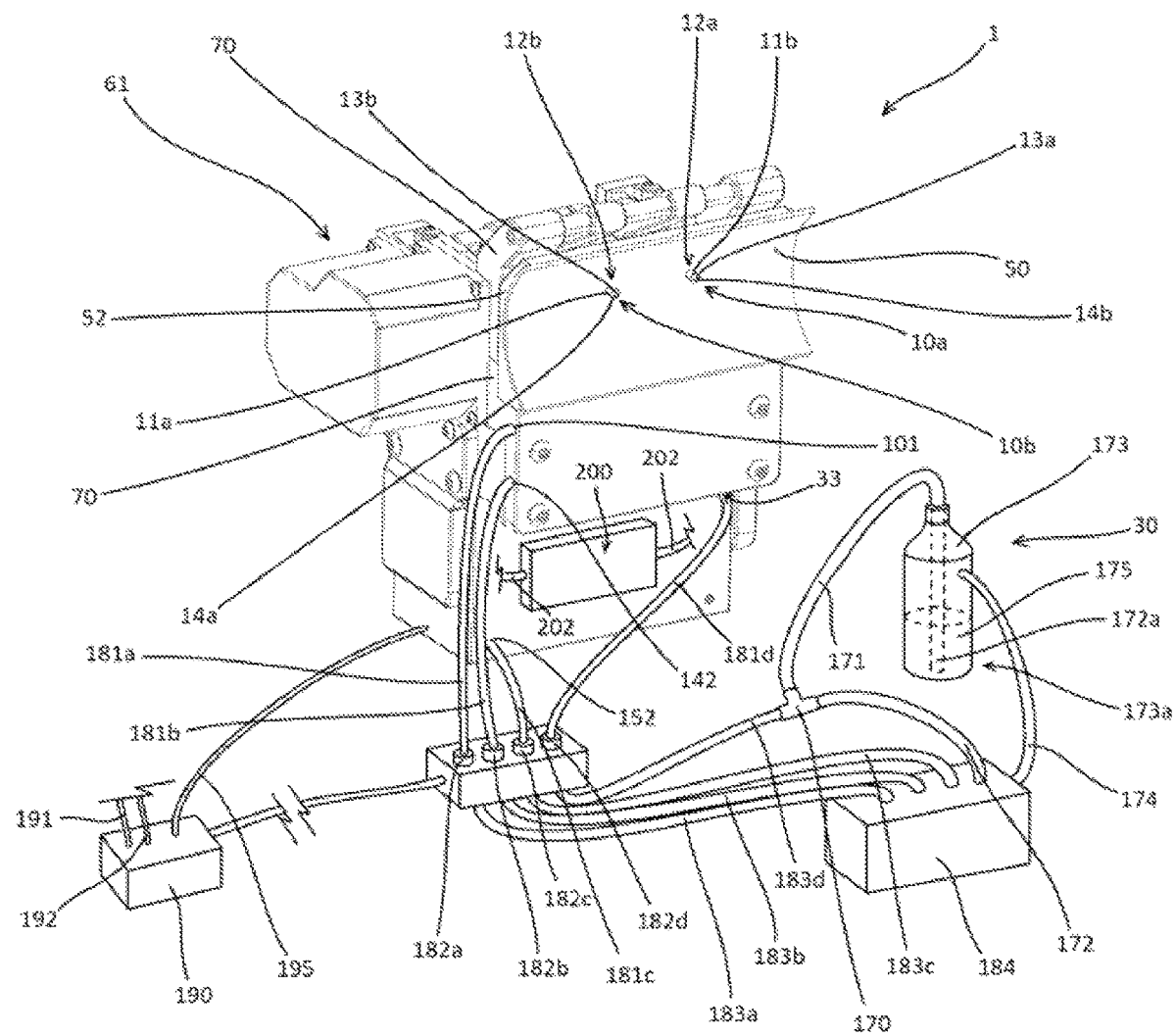
FIG. 2 is a rear perspective view of the sampler with the flushing device and the controller.
Figure 3:
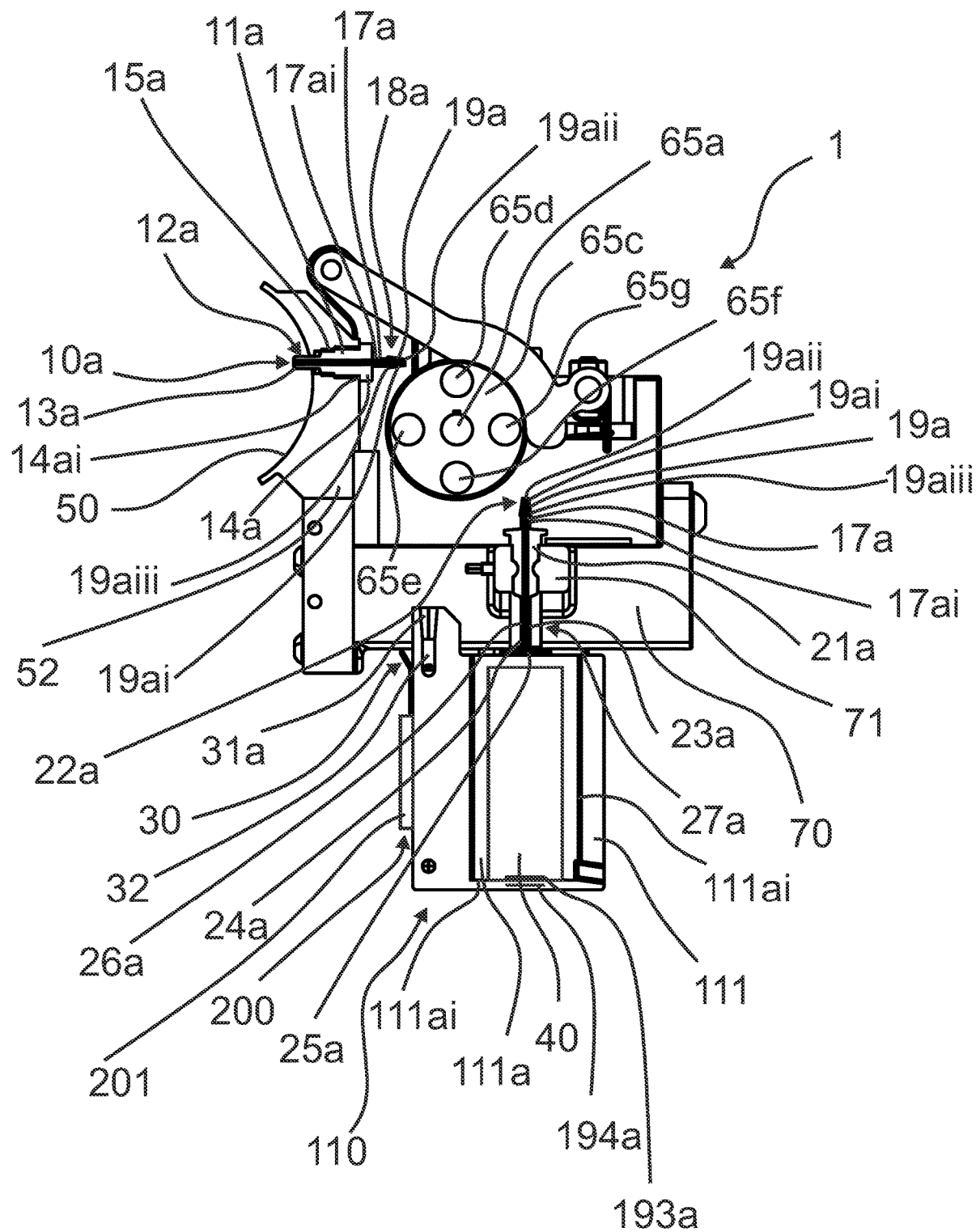
FIG. 3 is a left side cross-sectional view of the sampler through a first inlet pipe and a first outlet pipe without the flushing device, the controller and flexible tubes.

Preferred features of the present invention will now be described with particular reference to the accompanying drawings. However, it is to be understood that the features illustrated in and described with reference to the drawings are not to be construed as limiting on the scope of the invention.

A sampler 1 including an inlet 10a,b, an outlet 20 and a flushing device 30, the sampler 1 adapted such that a sample fluid flows from the inlet 10a,b, out the outlet 20 and into sample containers 40, wherein, the flushing device 30 is adapted to flush a pressurised flushing fluid past all surfaces of the sampler 1 which are adapted to contact the sample fluid.

The sampler 1 (sample dispenser) is adapted to be mounted on a sample fluid vessel. Preferably, the sampler 1 is adapted to be mounted on a pipe of the sample fluid vessel. Preferably, the sample fluid vessel is adapted such that sample fluid can flow between the pipe of the sample fluid vessel and a main tank of the sample fluid vessel.

The sampler 1 is adapted to be welded to the pipe of the sample fluid vessel. The sampler 1 includes a mounting surface 50 which follows a shape of an outer surface of the pipe of the sample fluid vessel where the sampler 1 is mounted. The mounting surface 50 is in the form of a segment of a cylinder and/or is cylindrical in shape. The mounting surface 50 is adapted to be welded to the pipe of the sample fluid vessel.

The sampler 1 includes a first inlet 10a and a second inlet 10b. The sample fluid vessel includes holes which are adapted to receive first and second outer ends 12a,b of the first and second inlet pipes 11a,b respectively. The outer ends 12a,b (first and second outer ends) of the inlet pipes 11a,b (first and second inlet pipes) protrude from the mounting surface 50. The outer ends 12a,b of the inlet pipes 11a,b are adapted to protrude through the holes in the sample fluid vessel and protrude into a cavity of the sample fluid vessel. This allows easier cleaning of the outer ends 12a,b of the inlet pipes 11a,b than if the ends of the inlet pipes were mounted sunken into an inner surface of the pipe of the sample fluid vessel. The outer ends 12a,b of the inlet pipes 11a,b include radiused outer edges 13a,b which also allows easier cleaning of the outer ends 12a,b of the inlet pipes 11a,b.

The outer ends 12a,b of the inlet pipes 11a,b form part of inlet inserts 14a,b which include threads 15a,b on outer surfaces of the inlet inserts 14a,b and are adapted to be screwed into a mounting body 52. The mounting body 52 including the mounting surface 50. The inlet inserts 14a,b each including a radial step 14ai,bi. The radial steps 14ai,bi are adapted to contact the mounting body 52 to limit the distance the inlet inserts 14a,b can be screwed into the mounting body 52 and provide a surface to tighten the inlet inserts 14a,b onto. The radial steps 14ai,bi include hexagonal outer surfaces 16a,b adapted to receive a tool such as a spanner to tighten the inlet inserts 14a,b into the mounting body 52. The radial steps 14ai,bi may include any surfaces adapted to receive a tool to turn the inlet inserts 14a,b.

The inlet inserts 14a,b include barbed pipes 17a,b on inner ends 18a,b of the inlet inserts 14a,b respectively. The inner ends 18a,b of the inlet inserts 14a,b are on an opposite end of the inlet inserts 14a,b to the outer ends 12a,b of the inlet inserts 14a,b. The barbed pipes 17a,b each include a single circumferential barb 19a,b (barb). The barbs 19a,b include angled surfaces 19ai,bi with a smaller diameter at tips 19aii,bii of the inner ends 18a,b and larger diameters increasing down the length of the barbed pipes 17a,b away from the tips 19aii,bii up to steps 19aiii,biii of the barbs 19a,b. The step 19aiii,biii steps down the diameter of the barbs 19a,b to a cylindrical portion 17ai,bi of each of the barbed pipes 17a,b.

Outlet inserts 21a,b are adapted to receive second ends 63a,b of flexible tubes 60a,b. The outlet inserts 21a,b include the same barbed pipes 17a,b as the inlet inserts 14a,b. The barbed pipes 17a,b of the inlet inserts 14a,b are adapted to receive first ends 62a,b of the flexible tubes 60a,b. The barbed pipes 17a,b of the outlet inserts 21a,b are adapted to receive second ends 63a,b of the flexible tubes 60a,b. The flexible tubes 60a,b are adapted to slide over the barbs 19a,b respectively with first ends 62a,b and second ends 63a,b of the flexible tubes 60a,b past the steps 19aiii, biii of the barbs 19a,b of the respective inlet inserts 14a,b and outlet inserts 21a,b. The barbs 19a,b are adapted to stretch the flexible tubes 60a,b such that the flexible tubes 60a,b on the barbs 19a,b form a sealed join. The flexible tubes 60a,b form part of a peristaltic pump 61. The flexible tubes 60a,b are adapted to be replaced every 2 to 4 days. Advantageously, the barbed pipes 17a,b only include a single circumferential barb 19a,b resulting in the barbed pipe 17a,b and flexible tube join not having cavity's that could potentially accumulate sample fluid from previous samples taken. The accumulation of sample fluid from previous samples could be released into future samples of sample fluid taken potentially resulting in incorrect measurements from tests of the sample fluid. For example, bacteria may grow in the accumulation of sample fluid and then higher levels of bacteria may be measured in testing samples of sample fluid than what is actually in the sample fluid taken from the sample fluid vessel.

The sampler 1 further includes a main body 70. The main body 70 includes multiple pieces attached together with bolts 70a. The main body 70 includes a bridge 71. The outlet inserts 21a,b are adapted to be removably inserted into the bridge 71. The outlet inserts 21a,b are adapted to be locked in first holes 73a,b in the bridge 71. Moveable shafts 28a,b are adapted to be located in second holes 74a,b in the bridge 71. Longitudinal axes of the moveable shafts 28a,b are adapted to be orientated perpendicular to longitudinal axes of the outlet inserts 21a,b. The moveable shafts 28a,b each include a cut out portion 29ai,bi and a cylindrical portion 29aii,bii of outer surfaces of the moveable shafts 28a,b. When the moveable shafts 28a,b are in an unlocked position, the cut out portions 29ai,bi are aligned with or closest to the outlet inserts 21a,b which results in the outlet inserts 21a,b having clearance to be removed from or inserted into the first holes 73a,b in the bridge 71. When the moveable shafts 28a,b are in a locked position, the cylindrical portions 29aii,bii are aligned with or closest to the outlet inserts 21a,b which results in the moveable shafts 28a,b blocking the outlet inserts 21a,b from being removed or inserted into or out of the first holes 73a,b in the bridge 71. Springs 75a,b are adapted to be positioned between the bridge 71 and the moveable shafts 28a,b. The springs 75a,b are adapted to force the moveable shafts 28a,b into the locked position. The moveable shafts 28a,b extend out of the bridge 71 and are adapted to be actuated manually by being pressed to move the moveable shafts 28a,b from the locked position to the unlocked position. The barbed pipes 17a,b are located on an upper end 22a,b of the outlet inserts 21a,b. A lower end 27a,b of the outlet inserts 21a,b includes needles 23a,b. The needles 23a,b each include a tapered outer surface 24a,b from a smaller outer diameter tip 25a,b of the needles 23a,b to a larger outer diameter cylindrical portion 26a,b of the needles 23a,b which is further up a length of the needles 23a,b.

The peristaltic pump 61 also includes a motor 64 mounted to the main body 70 which is engaged with and adapted to rotate a rotating member 65. The rotating member 65 includes a central shaft 65a, two end plates 65b,c and four rods 65d-g (rods). The central shaft 65a is coaxial with and engaged with an output shaft 64a of the motor 64. The motor 64 may be a stepper motor, a servo motor or another motor which can rotate the output shaft 64a to a certain angle with an accuracy of for example +−10 degrees. The two end plates 65b,c are adapted to be mounted on and rotate with the central shaft 65a. The four rods 65d-g each include a first end 66a attached to bearings 67 inside a first end plate 65b of the two end plates 65b,c and a second end 66b attached to bearings 67 inside a second end plate 65c of the two end plates 65b,c. Therefore, the rods 65d-g rotate relative to the two end plates 65b,c. Each of the rods 65d-g are adapted to be positioned at the same radial location on the end plates 65b,c and spaced evenly around the end plates 65b,c. The rods 65d-g are adapted to be positioned such that shortest distances between longitudinal axis of the rods 65d-g are equal between adjacent rods 65d-g.

The peristaltic pump 61 further includes clamps 80a,b adapted to provide a contact surface 81a,b to removably contact the flexible tubes 60a,b. The clamps 80a,b are in the form of arms. The flexible tubes 60a,b are adapted to be positioned between the rods 65d-g and the clamps 80a,b. In a pumping position and when pumping, the contact surface 81a,b of the clamps 80a,b are concentric with a path of rotation of longitudinal axis of the rods 65d-g and with the central shaft 65a. In the pumping position, the flexible tubes 60a,b are adapted to be compressed between the clamps 80a,b and at least one of the rods 65d-g at a time. When pumping, the rods 65d-g are adapted to rotate about the central shaft 65a and roll, not slide along the flexible tubes 60a,b. When pumping, at least one of the rods 65d-g are adapted to first compress portions of the flexible tubes 60a,b between at least one of the rods 65d-g and the clamps 80a,b at a time. Preferably, when pumping, at least one of the rods 65d-g are adapted to first compress portions of the flexible tubes 60a,b between the at least one of the rods 65d-g at a time and the clamps 80a,b. Then, during pumping, at least one of the rods 65d-g at a time are adapted to roll towards the second ends 63a,b of the flexible tubes 60a,b therefore moving the compressed portions of the flexible tubes 60a,b towards the second ends 63a,b of the flexible tubes 60a,b. This process is adapted to pump sample fluid from the inlet 10 to and out the outlet 20. The sample fluid is then adapted to flow out of the outlet into the sample containers 40. In the following passage, references to a "selected flexible tube 60a,b" refers to one of any one of the flexible tubes 60a,b. A length of the selected flexible tube 60a,b which is adapted to contact the rods 65d-g may be any length compared to a sum of other lengths of the selected flexible tube which is not adapted to contact the rods 65d-g. The length of the selected flexible tube 60a,b which is adapted to contact the rods 65d-g may be above 30% of the sum of the lengths of the selected flexible tube 60a,b which is not adapted to contact the rods 65d-g. Preferably, the length of the selected flexible tube 60a,b which is adapted to contact the rods 65d-g is at least half the sum of lengths of the selected flexible tube 60a,b which are adapted not to contact the rods 65d-g. Preferably, the length of the selected flexible tube 60a,b which is adapted to contact the rods 65d-g is at least ⅓ of a full length of one of the flexible tubes 60a,b.

Figure 4:
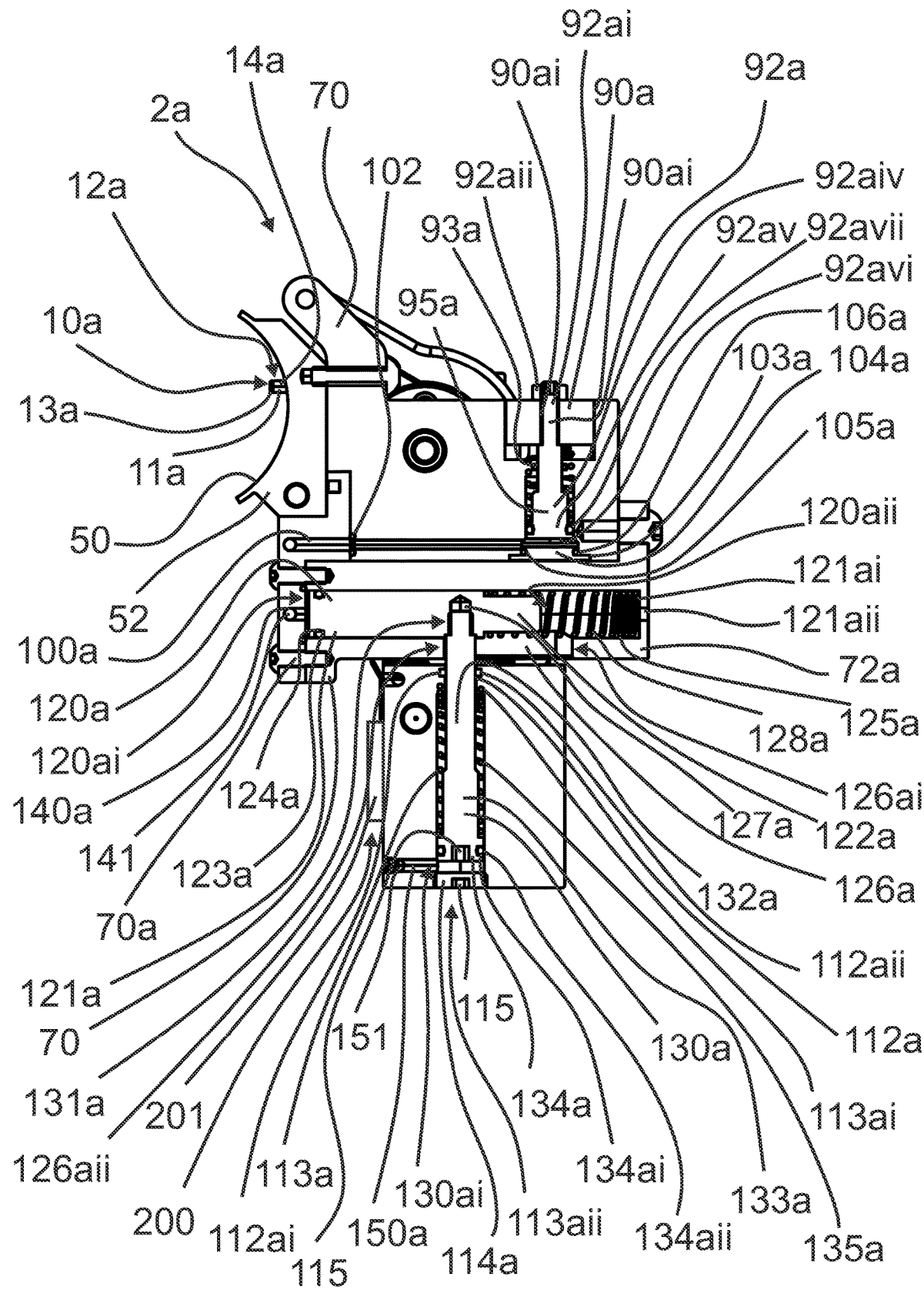
FIG. 4 is a left side cross-sectional view of the sampler through a first piston of a first set of pistons, a first piston of a second set of pistons and a first piston of a third set of pistons without the flushing device or the controller.
Figure 5:
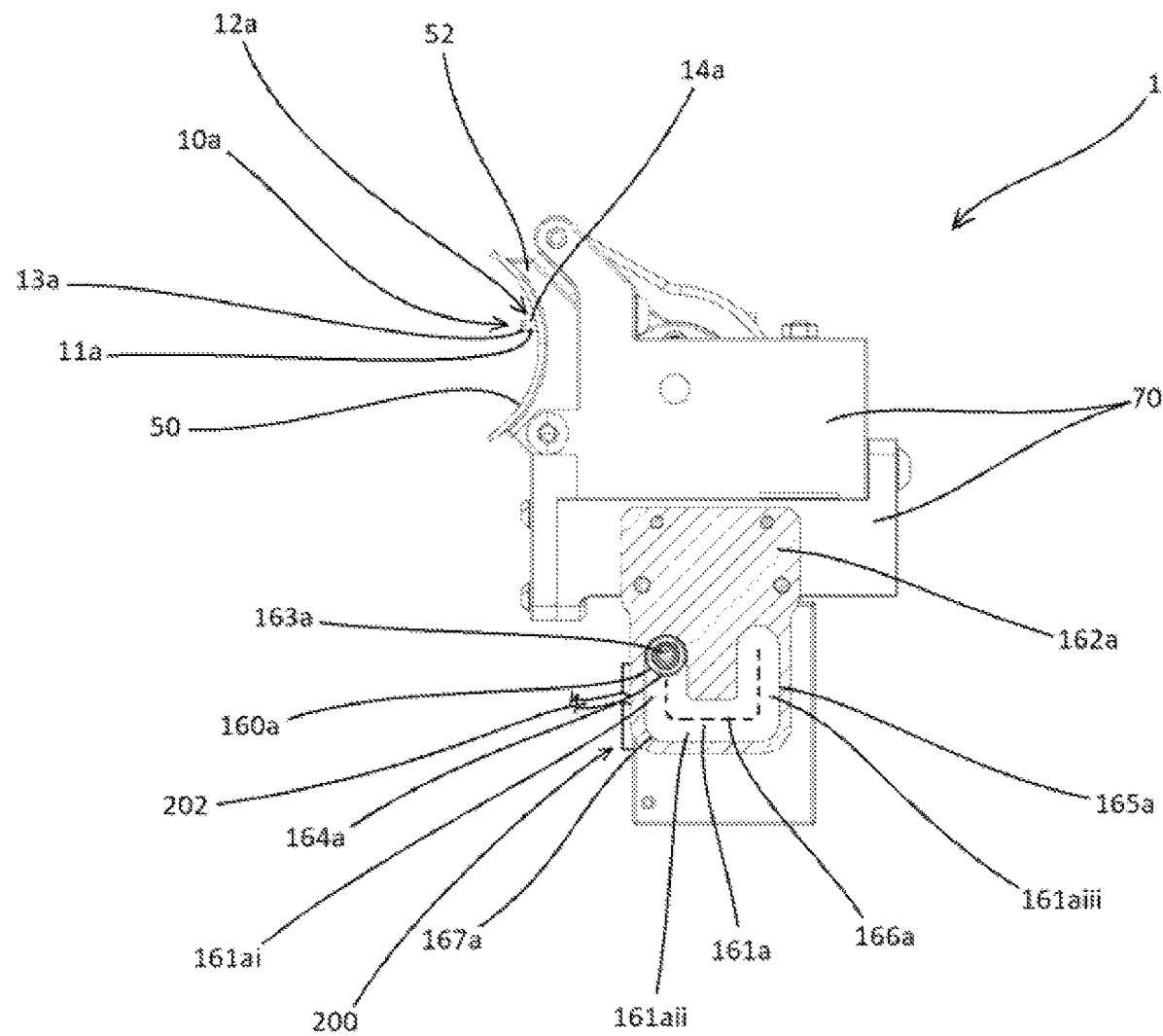
FIG. 5 is a left side cross-sectional view of the sampler through a first bearing channel block without the flushing device and the controller.
Figure 6:
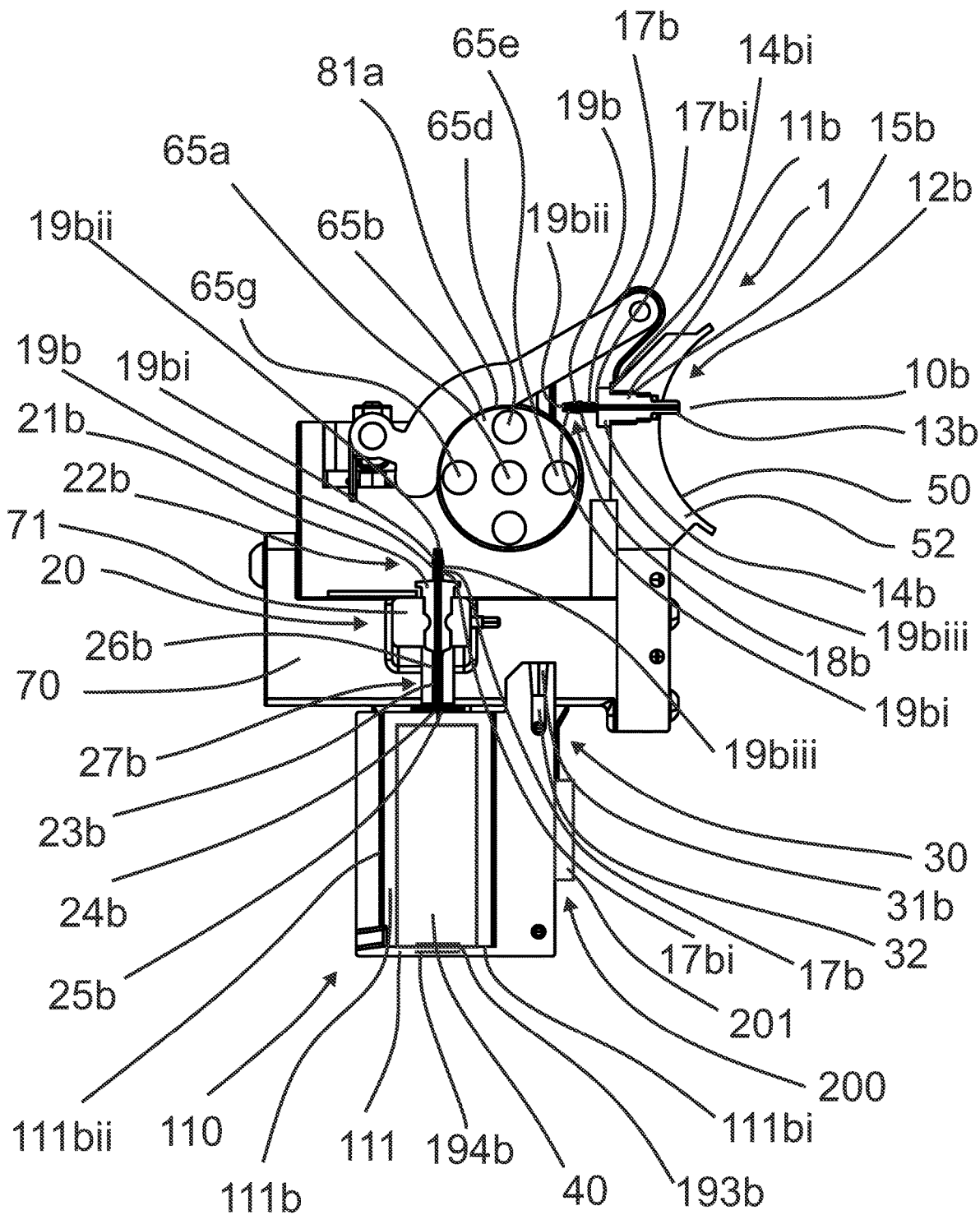
FIG. 6 is a right side cross-sectional view of the sampler through a second inlet pipe and a second outlet pipe without the flushing device, the controller and the flexible tubes.
Figure 7:
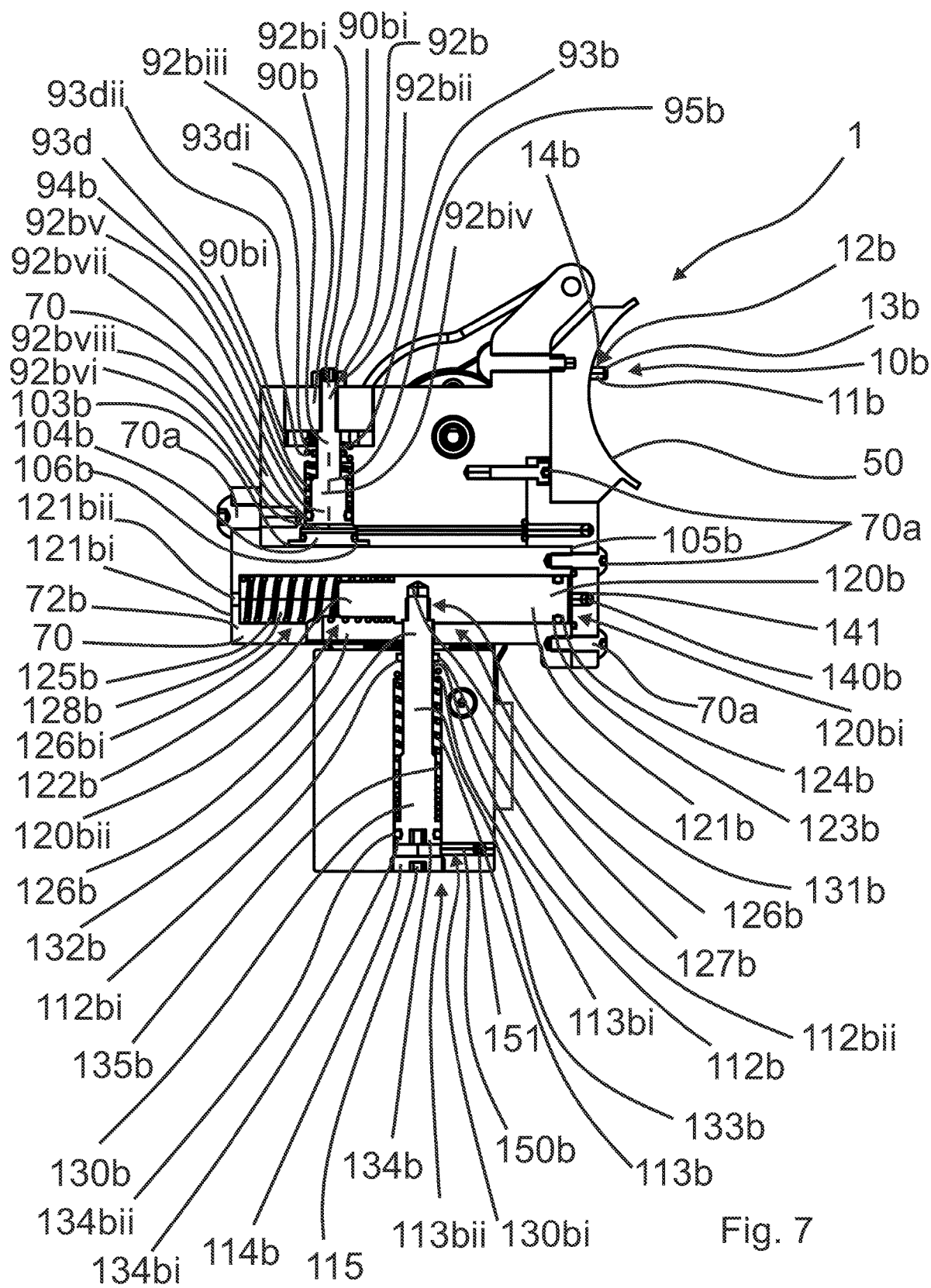
FIG. 7 is a right side cross-sectional view of the sampler through a second piston of the first set of pistons, a second piston of the second set of pistons and a second piston through the third set of pistons without the flushing device and the controller.
Figure 8:
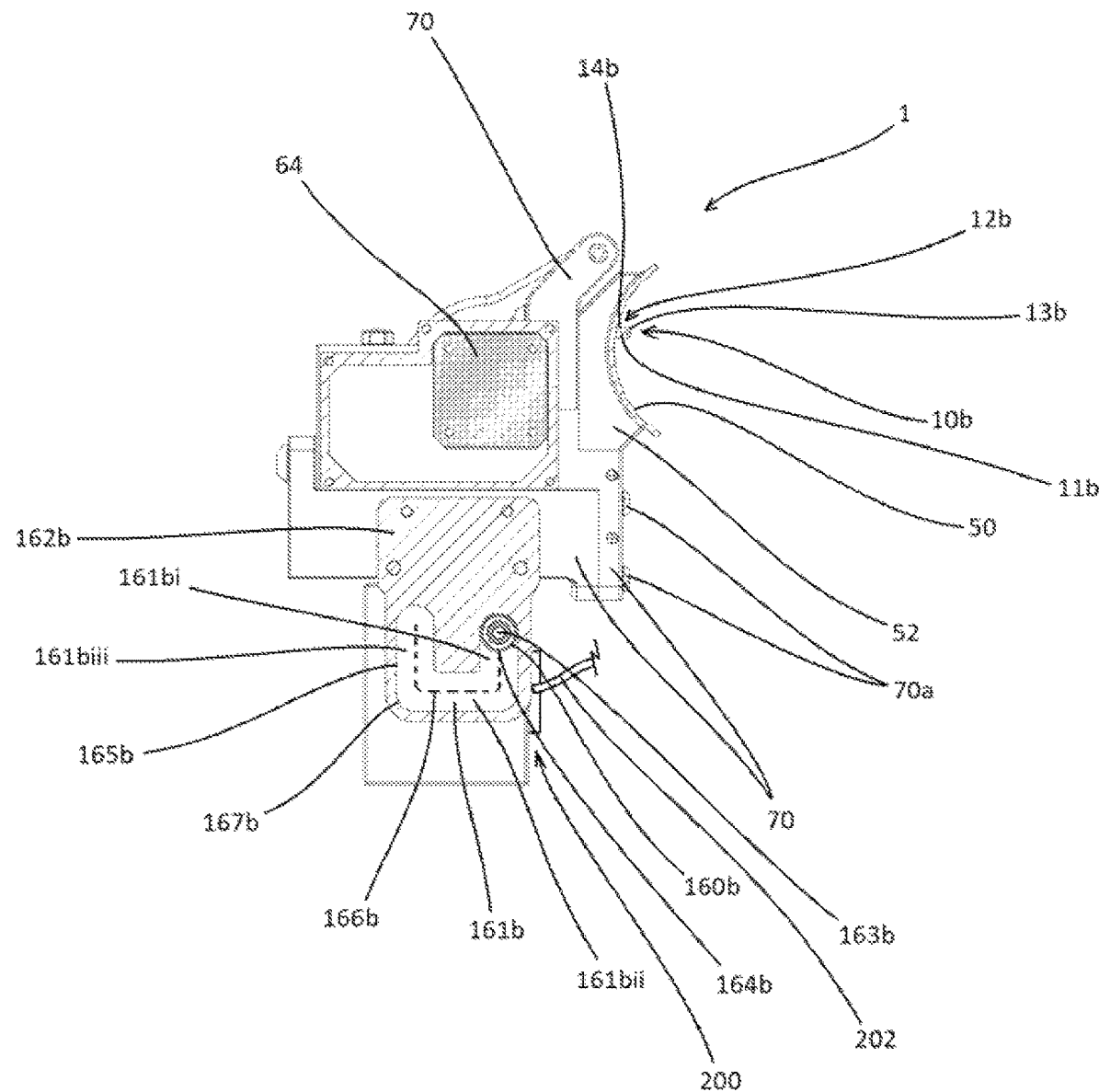
FIG. 8 is a right side cross-sectional view of the sampler through a second bearing channel block without the flushing device and the controller.
Figure 9:
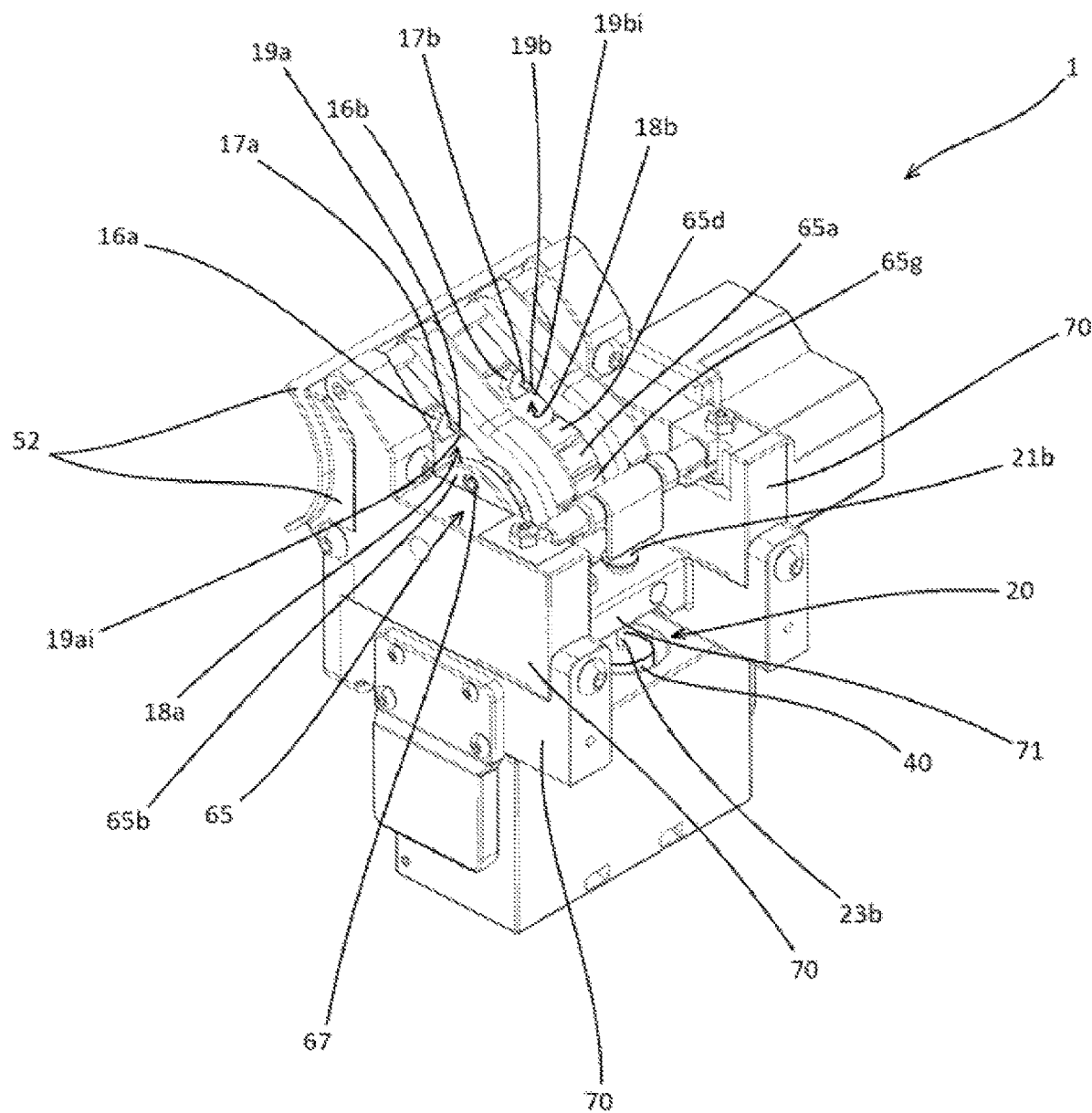
FIG. 9 is a front perspective view of the sampler without the flushing device, the controller and the flexible tubes.
Figure 10:
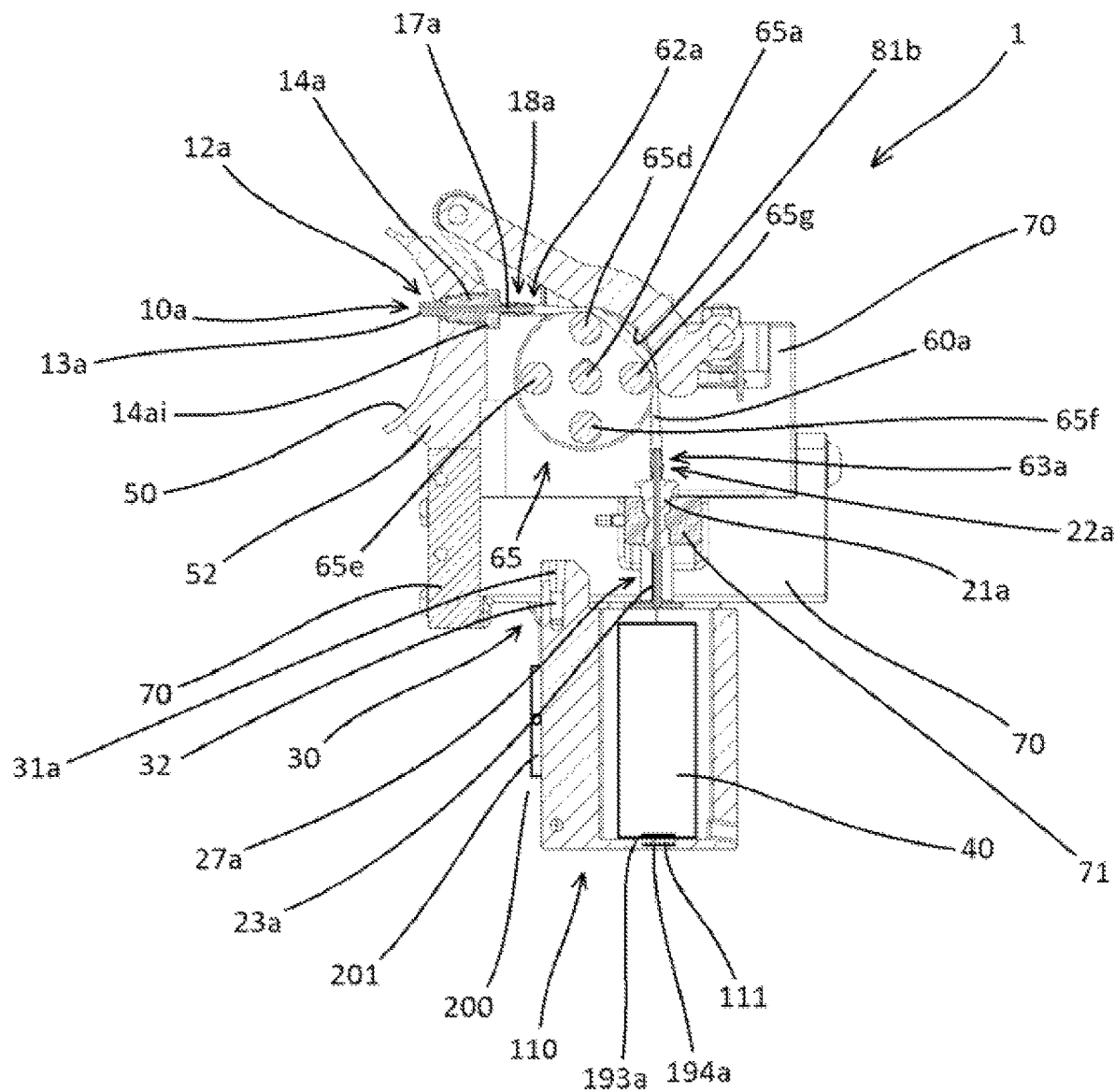
FIG. 10 is a left side cross-sectional view of the sampler through the first inlet pipe and the first outlet pipe without the flushing device and the controller and with the flexible tubes.
Figure 11:
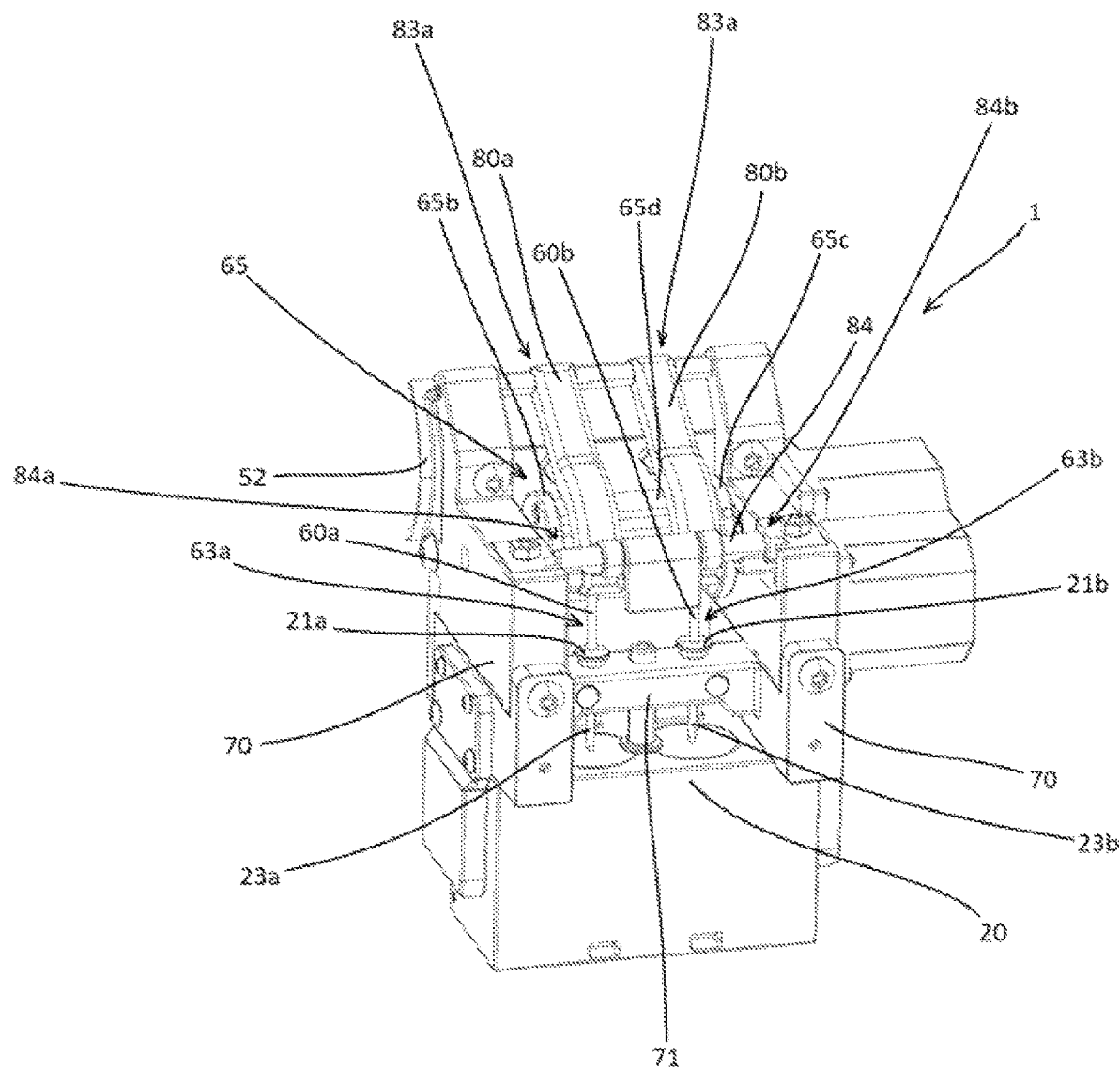
FIG. 11 is a front perspective view of the sampler without the flushing device and the controller and with the flexible tubes.
Figure 12:
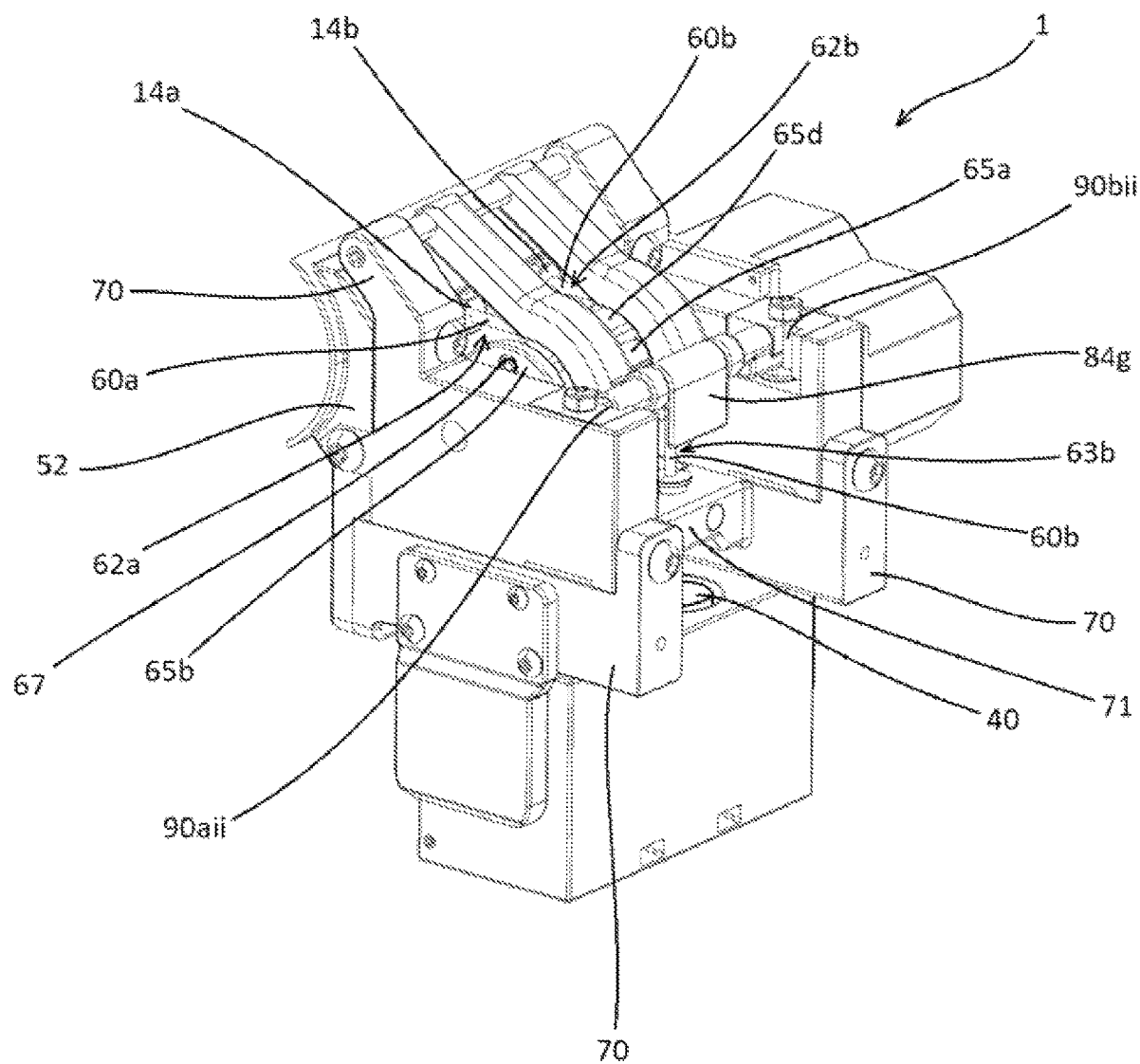
FIG. 12 is a left perspective view of the sampler without the flushing device and the controller and with the flexible tubes.
Figure 13:
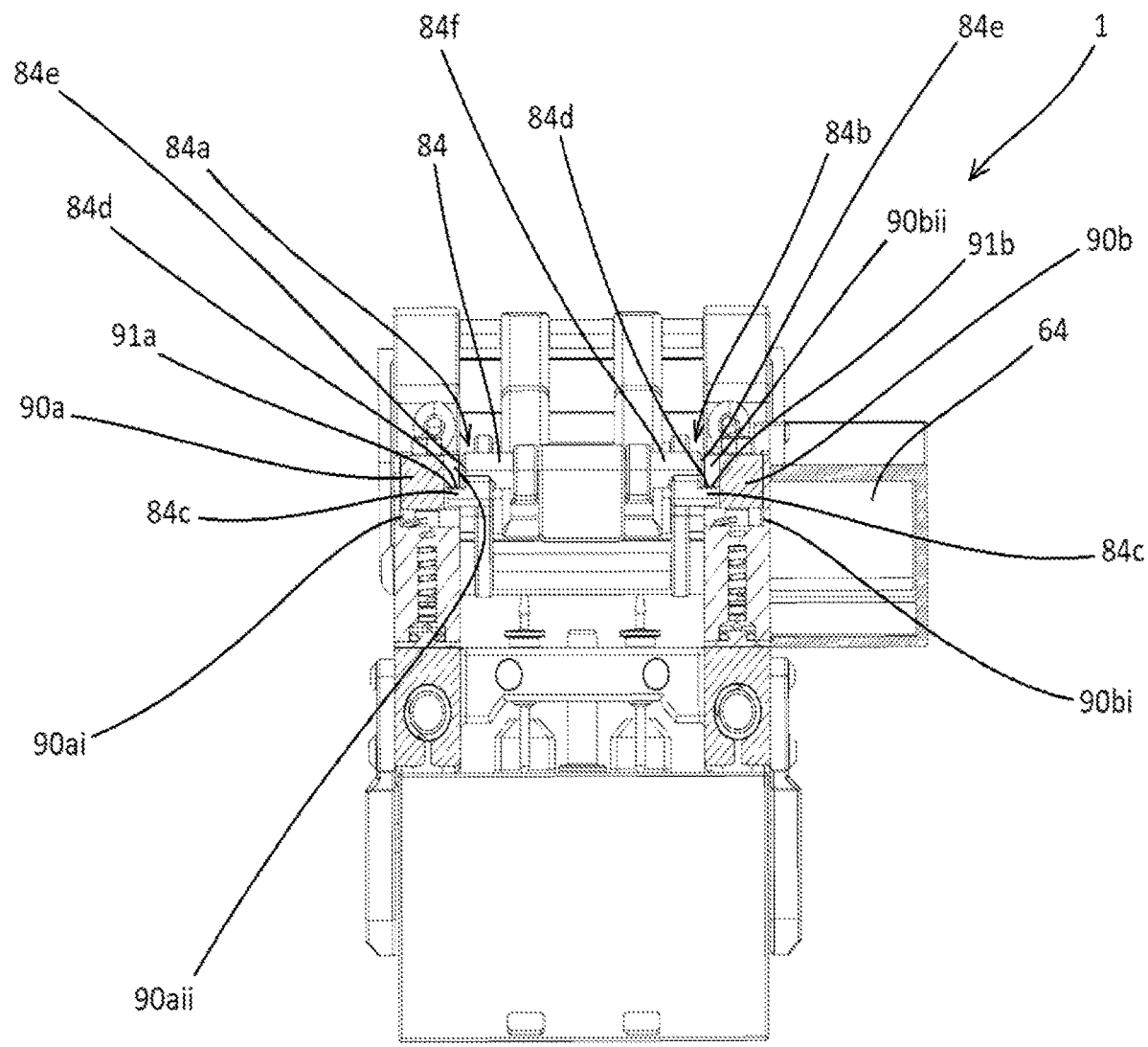
FIG. 13 is a front cross-sectional view of the sampler through sliding members without the flushing device and the controller.
Figure 14:
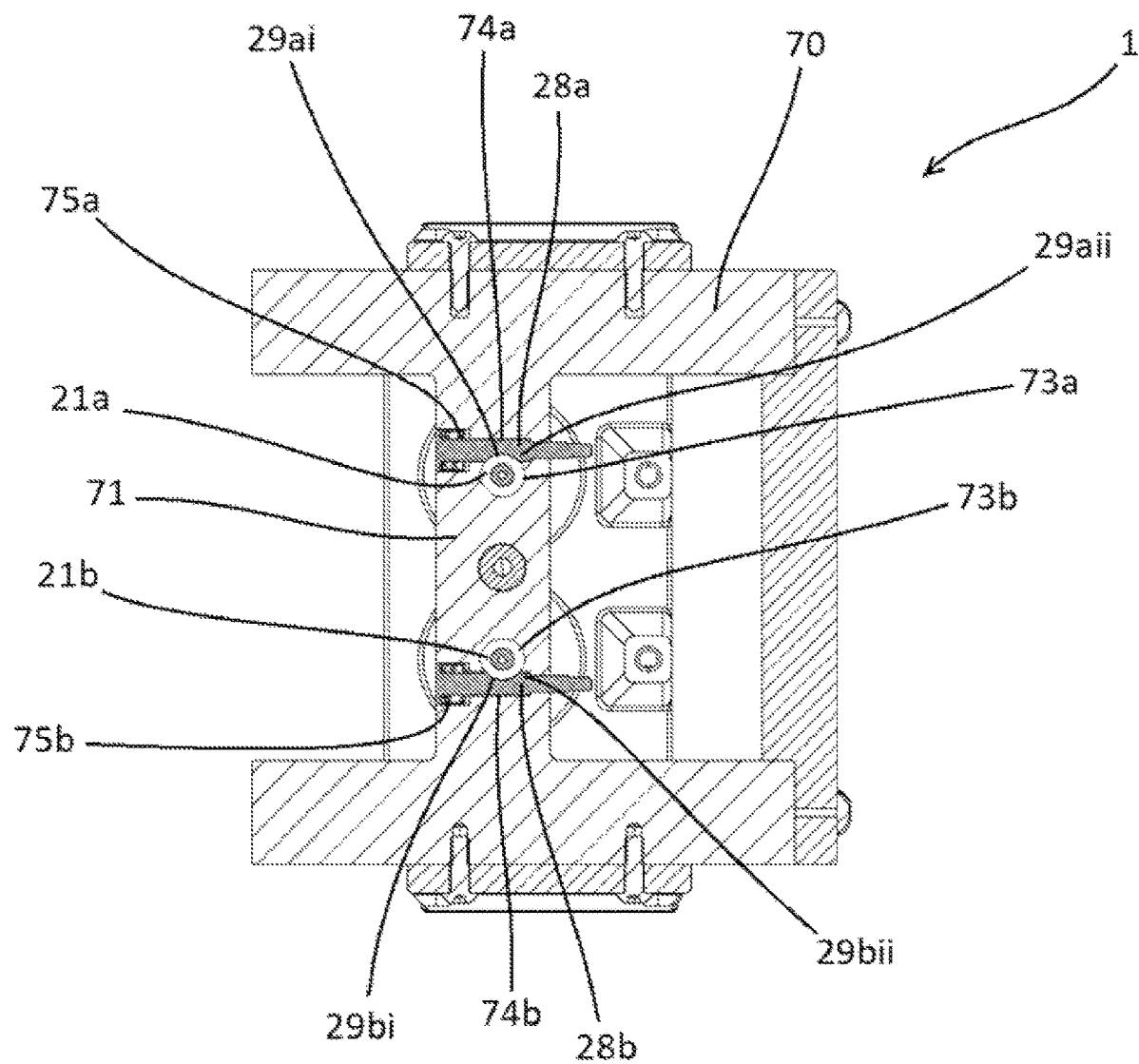
FIG. 14 is a top cross-sectional view of the main body of the sampler without the flushing device and the controller.

The clamps 80a,b are adapted to be moved away from the flexible tubes 60a,b such that the contact surface 81a,b does not contact the flexible tubes 60a,b. Upper ends 83a of the clamps 80a,b are mounted on and adapted to rotate about an upper arm axle 82. The upper arm axle 82 is fixed to and spans between two portions of the main body 70. Lower ends 83b of the clamps 80a,b are mounted on and adapted to rotate relative to a lower arm axle 84. Each end 84a,b of the lower arm axle 84 includes a lower arm axle arm 84c extending radially from a longitudinal axis of the lower arm axle 84 and then parallel to the longitudinal axis of the lower arm axle 84 as seen in FIG. 13. Lower contact surfaces 91a,b of sliding members 90a,b contact upper contact surfaces 84d of the lower arm axle arm 84c such that the upper contact surfaces 84d cannot move above the lower contact surfaces 91a,b of the sliding members 90a,b. Furthermore, ends 84e of a cylindrical portion 84f of the lower arm axle 84 abut the sliding members 90a,b therefore limiting axial movement of the lower arm axle 84. The sliding members 90a,b are adapted to move perpendicular to the lower contact surfaces 91a,b in sliding member channels 90ai,bi. The sliding members 90a,b are fixed to a first set of pistons 92a,b which have longitudinal axes 95a,b perpendicular to the lower contact surfaces 91a,b and are each adapted to slide in first channels 93*a,b* and second channels 93*c,d* as seen in FIGS. 4 and 7. The first set of pistons 92*a,b* are pneumatically actuated pistons. The first and second channels 93*a-d* are cylindrical. The pistons of the first set of pistons 92*a,b* each include a threaded shaft 92*ai,bi* and a first portion 92*aiii,biii* below the threaded shafts 92*ai,bi*. The threaded shafts 92*ai,bi* are adapted to be inserted through holes 90*ai,bi* in the sliding members 90*a,b*. The first portion 92*aiii,biii* has a larger diameter than the threaded shaft 92*ai,bi* and the holes 90*ai,bi*. Nuts 92*aii,bii* are adapted to screw onto the threaded shafts 92*ai,bi* therefore compressing the sliding members 90*a,b* against the first portion 92*aiii,biii* and fixing each of the sliding members 90*a,b* to their respective first set of pistons 92*a,b*. The first channels 93*a,b* include internal circumferential slots 93*ci,di* with O-rings 93*cii,dii*. The O-rings 93*cii,dii* form a seal between the first channels 93*a,b* and the first portions 92*aiii,biii* of the first set of pistons 92*a,b*. The first portions 92*aiii,biii* include diameters substantially the same as the first channels 93*a,b*. Therefore, the first channels 93*a,b* are adapted to guide the first set of pistons 92*a,b* to travel linearly along the longitudinal axes 95*a,b* of the first set of pistons 92*a,b*. Third portions 92*av,bv* of the first set of pistons 92*a,b* are below second portions 92*aiv,biv* and include a larger diameter than the second portions 92*aiv,biv*. The second channels 93*c,d* are below and connected to the first channels 93*a,b*. The second portions 92*aiv,biv* and the third portions 92*av,bv* are adapted to be contained within the second channels 93*c,d*. The third portions 92*av,bv* include a maximum diameter substantially the same as internal diameters of the second channels 93*c,d*.

Substantially being within 10% of the diameter. Therefore, the third portions 92*av,bv* of the first set of pistons 92*a,b* also slide along and are guided by the second channels 93*c,d*. The second portions 92*aiv,biv* include a diameter larger than the first channels 93*a,b* and therefore cannot go through the first channels 93*a,b*. Therefore, the first set of pistons 92*a,b* and the sliding members 90*a,b* cannot go above a certain height. Springs 94*a,b* are adapted to be located between the first and second portions 92*aiii,biii,aiv,biv* and the second channels 93*c,d*. The springs 94*a,b* are compressed between the third portions 92*av,bv* and upper ends 96*a,b* of the second channels 93*c,d*. Therefore, the springs 94*a,b* apply a downward force onto the first set of pistons 92*a,b*, the sliding members 90*a,b* and the lower arm axle 84. Since the lower contact surfaces 91*a,b* of the sliding members 90*a,b* contact and are above upper contact surfaces 84*d* of the lower arm axle arm 84*c*, the downward force applied by the springs 94*a,b* applies a downwards force to the clamps 80*a,b* and therefore compresses the flexible tube between the clamps 80*a,b* and at least one of the rods 65*d-g* at a time. The sampler 1 may be adapted to automatically or manually release the clamps 80*a,b* and automatically or manually move the clamps 80*a,b* away from the flexible tubes 60*a,b*. Preferably, the sampler 1 is adapted to include manual actions and automatic pneumatic methods to release the clamps 80*a,b* so they can be manually moved away from the flexible tubes 60*a,b*. The third portions 92*av,bv* include circumferential slots 92*avii,bvii* each adapted to receive an O-ring 92*aviii,bviii*. The O-rings 92*aviii,bviii* are adapted to create a seal between the third portions 92*av,bv* and the second channels 93*c,d*. Lower end faces 92*avi,bvi* of the third portions 92*av,bv* form walls of a first set of sealed channels 100*a,b*. The first sealed channels 100*a,b* are in fluid communication with a first valve 182*a* of a set of valves. The first valve 182*a* is also in fluid communication with a pressurized air source 184. The pressurized air source may be a compressed air tank, air compressor or other pressurized air sources. The first sealed channels 100*a,b* include holes through the main body 70 and the mounting body 52. The first sealed channels 100*a,b* include O-rings 102 located between and adapted to seal joining faces between the main body 70 and the mounting body 52 in locations where the first sealed channels 100*a,b* includes a hole through the main body 70 which connects to a hole through the mounting body 52. The first sealed channels 100*a,b* include assembly holes 103*a,b* underneath and coaxial with the second channels 93*c,d*. The assembly holes 103*a,b* are adapted to receive the first set of pistons 92*a,b* for example during assembly. Smallest internal diameters of the assembly holes 103*a,b* are larger than the diameter of the second channels 93*c,d*. The assembly holes 103*a,b* are each adapted to receive a first plug 104*a,b*. The first plugs 103*a,b* are adapted to seal and plug the assembly holes 103*a,b*. The first plugs 103*a,b* each include an external slot 105*a,b* with an O-ring 106*a,b* which are adapted to create a seal between the assembly holes 103*a,b* and the first plugs 104*a,b*. The first set of pistons 92*a,b* includes a first piston 92*a* on a first side 2*a* of the sampler 1 and a second piston 92*b* on a second side 2*b* of the sampler 1. Unless otherwise stated, the above descriptions of the sliding members 90*a,b*, first set of pistons 92*a,b*, nuts 92*aii,bii*, springs 94*a,b*, O-rings 93*cii,dii*, 92*aviii,bviii* and features of these components are referring to two components with one of the components with a "a" in it's reference on the first side 2*a* of the sampler 1 and another symmetrical component with a "b" in its reference on the second side 2*b* of the sampler 1. The first set of sealed channels 100*a,b* include a first sealed channel 100*a* and a second sealed channel 100*b*. The lower end face 92*avi* of the third portion 92*av* of the first piston 92*a* of the first set of pistons 92*a,b* forms a wall of the first sealed channel 100*a* of the first set of sealed channels 100*a,b*. The lower end face 92*bvi* of the third portion 92*bv* of the second piston 92*b* of the first set of pistons 92*a,b* forms a wall of the second sealed channel 100*b* of the first set of sealed channels 100*a,b*. The first and second sealed channels 100*a,b* of the first set of sealed channels 100*a,b* are separate through the main body 70 and join together in the mounting body 52. A first port 101 of the first set of sealed channels 100*a,b* is adapted to connect to a first tube 181*a* of the first set of sealed channels 100*a,b* which connects to the first valve 182*a*. The sampler 1 is adapted such that when the first valve 182*a* releases pressurized air into the first set of sealed channels 100*a,b*, a pressure differential between the lower end faces 92*avi,bvi* and other axially facing faces of the first set of pistons 92*a,b* applies a vertical force to the first set of pistons 92*a,b*. The vertical force applied to the first set of pistons 92*a,b* raises the sliding member 90*a,b* to a raised position which is where the second portions 92*aiv,biv* contact the upper ends 96*a,b* of the second channels 93*c,d*. The lower arm axle 84 includes a rigid panel 84*g* extending tangent to a circumference of the lower arm axle 84. The rigid panel 84*g* may be any component fixed to the lower arm axle 84 capable of being manually operated to rotate and move the lower arm axle 84. With the sliding member 90*a,b* in the raised position, an operator can rotate the rigid panel 84, rotating the lower arm axle 84 until the lower arm axle arms 84*c* are in release slots 90*aii,bii* of the sliding members 90*a,b*. Then the operator may lift the rigid panel 84*g* and/or the lower arm axle 84 until the lower arm axle arms 84*c* are out of the release slots 90*aii,bii*. The clamps 80*a,b* may then be rotated 180 degrees and rest on the mounting body 52. With the clamps 80*a,b* not on the flexible tubes 60*a,b*, the flexible tubes 60*a,b* can easily be accessed to be checked and/or replaced and/or other maintenance may be performed on the sampler 1. With the clamps 80a,b not compressing the flexible tubes 60a,b a flushing process may be carried out. The flushing process being where the flushing device 30 is adapted to flush the pressurised flushing fluid past all surfaces of the sampler 1 which are adapted to contact the sample fluid. It should be noted that the clamps 80a,b may not be required to be rotated 180 to carry out the flushing process but may only require that the sliding member 90a,b is in the raised position and therefore, the clamps are not compressing the flexible tubes 60a,b. After maintenance and/or the flushing process, the lower arm axle arms 84c can then be slotted back through the release slots 90aii,bii under the lower contact surfaces 91a,b of the sliding members 90a,b and the first valve 182a can be actuated to stop passing pressurized air into the first sealed channels 100a,b, moving the sliding member 90a,b back down so that the lower contact surfaces 91a,b of sliding members 90a,b contact upper contact surfaces 84d of the lower arm axle arm 84c. Therefore locking the lower arm axle arms 84c back under the sliding members 90a,b and compressing the flexible tubes 60a,b between the clamps 80a,b and the rotating member 65. The first valve 182a is connected to the pressurized air source 184 through a tube 183a. The pressurized air source 184 provides pressurized air to the first valve 182a.

The outlet 20 is adapted to dispense the pumped sample fluid from the needles 23a,b into the sample containers 40. A sample holder 110 is adapted to hold the sample containers 40. The sample holder 110 includes a block 111 which includes two holes 111a,b adapted to hold the sample containers 40. The two holes 111a,b are substantially cylindrical. The block 111 further includes a drainage hole 116a,b connected to each of the two holes 111a,b. The drainage holes 116a,b are adapted to allow fluid to flow out of the two holes 111a,b when for example water from rain builds up in the holes 111a,b. The holes 111a,b do not extend through the whole block 111 but include a base 111ai,bi adapted to support the sample containers 40. Preferably, the holes 111a,b include a non-stick lining 111aii,bii on cylindrical surfaces of the holes 111a,b such as Teflon. When the block 111 is in a dispensing position the needles 23a,b are coaxial with the two holes 111a,b. The block 111 further includes two flushing ports 31a,b forming part of the flushing device 30 and adapted to receive the needles 23a,b. The block 111 is moveable to selectively align either the two holes 111a,b of the block 111 under the needles 23a,b or the two flushing ports 31a,b over and coaxial with the needles 23a,b. The block 111 is moveable along two axes. A first axis of the two axes is parallel with longitudinal axes of the first and second inlet pipes 11a,b and a second axis of the two axes is parallel with longitudinal axes of the outlet inserts 21a,b. The first axis is orientated in an upward and downward direction and the second axis is orientated in a frontward and backward direction in this specification. The block 111 is actuated with pneumatically actuated pistons.

A second set of pistons 120a,b are adapted to actuate the frontward and backward direction of the block 111 and a third set of pistons 130a,b are adapted to actuate the upward and downward direction. The second set of pistons 120a,b includes a first piston 120a on the first side 2a of the sampler 1 and a second piston 120b on the second side 2b of the sampler 1. The third set of pistons 130a,b also includes a first piston 130a on the first side 2a of the sampler 1 and a second piston 130b on the second side 2b of the sampler 1. The second set of pistons 120a,b include longitudinal axes aligned in the frontward and backward direction and the third set of pistons 130a,b include longitudinal axes aligned in the upward and downward direction.

The second set of pistons 120a,b are adapted to be located in third channels 128a,b. Both pistons of the second set of pistons 120a,b include a first portion 121a,b and a second portion 122a,b. The first portions 121a,b include an outer diameter substantially equal to an internal diameter of the third channels 128a,b. Substantially being +−10%. Therefore the first portions 121a,b slide through and are guided by the third channels 128a,b. The first portions 121a,b each include a circumferential slot 123a,b adapted to receive an O-ring 124a,b. The O-rings 124a,b are adapted to create a seal between the first portions 121a,b and the third channels 128a,b. The second portions 122a,b include a smaller outer diameter than the first portions 121a,b creating space between the second portions 122a,b and the third channels 128a,b. Springs 125a,b are adapted to be partially located in and extend from the space between the second portions 122a,b and the third channels 128a,b and into other spaces of the third channels 128a,b. The springs 125a,b are adapted to be compressed between the first portions 120a,b and first end walls 121ai,bi of the third channels 128a,b. The springs 125a,b are adapted to force the second set of pistons 120a,b backwards which is towards the mounting body 52. The first end walls 121ai,bi of the third channels 128a,b both include a hole 121aii,bii. The holes 121aii,bii are adapted to vent the third channels 128a,b during axial movement of the second set of pistons 120a,b. The third channels 128a,b further include a third channel slot 126a,b which extends downward all the way through walls 72a,b of the main body 70 and runs frontwards and backwards or parallel to a longitudinal axis of the second set of pistons 120a,b.

The first piston 130a of the third set of pistons 130a,b is adapted to be fixed to and aligned perpendicular to the first piston 120a of the second set of pistons 120a,b. The second piston 130b of the third set of pistons 130a,b is adapted to be fixed to and aligned perpendicular to the second piston 120b of the second set of pistons 120a,b. Longitudinal axes of the third set of pistons 130a,b is adapted to be perpendicular to the longitudinal axes of the second set of pistons 120a,b. A threaded end 131a of the first piston 130a of the third set of pistons 130a,b is adapted to be screwed into a threaded hole 127a of the first piston 120a of the second set of pistons 120a,b. A threaded end 131b of the second piston 130b of the third set of pistons 130a,b is adapted to be screwed into a threaded hole 127b of the second piston 120b of the second set of pistons 120a,b. The block 111 includes fourth channels 112a,b and fifth channels 113a,b. The first and second piston 130a,b of the third set of pistons 130a,b each include a first portion 132a,b, a second portion 133a,b and a third portion 134a,b. The first portion 132a,b is adapted to be above the second portion 133a,b which is adapted to be above the third portion 134a,b. The first portion 132a,b is adapted to slide in and be guided by the fourth channel 112a,b. An inner diameter of the fourth channel 112a,b is substantially the same as an outer diameter of the first portion 132a,b of the third set of pistons 130a,b. Substantially being within 10%. The fourth channels 112a,b include internal slots 112ai,bi adapted to receive O-rings 112aii,bii. The O-rings 112aii,bii are adapted to create a seal between the first portions 132a,b of the third set of pistons 130a,b and the fourth channels 112a,b. The third portions 134a,b of the third set of pistons 130a,b are adapted to slide in an be guided by the fifth channel 113a,b. Internal diameters of the fifth channel 113a,b are substantially the same as external diameters of the third portion 134a,b of the third set of pistons 130a,b. Substantially being within 10%. The third portions 134a,b each include an external slot 134ai,bi adapted to receive an O-ring 134aii,bii. The O-ring is adapted to create a seal between the third portions 134a,b of the third set of pistons 130a,b and the fifth channel 113a,b. A spring 135a,b is adapted to be positioned between the first and second portions 132a,b, 133a,b of the third set of pistons 130a,b and the fifth channel 113a,b. The spring 135a,b is adapted to be compressed between the third portion 134a,b and an top faces 113ai,bi of the fifth channel 113a,b. Since the pistons of the third set of pistons 130a,b are each fixed to one of the pistons of the second set of pistons 120a,b and the second set of pistons 120a,b do not move upwards or downwards, the springs 135a,b are adapted to force the block 111 upwards. The fifth channel 113a,b extends all the way through open ends 113aii,bii of the fifth channel 113a,b at a bottom of the block 111. This allows assembly of the third set of pistons 130a,b into the block 111. The open ends 113aii,bii of the fifth channel 113a,b are adapted to be plugged with second plugs 114a,b. The second plugs 114a,b include threads adapted to engage with threads on the open ends 113aii,bii of the fifth channels 113a,b. The second plugs 114a,b and sealed channel ends 130ai,bi of the third set of pistons 130a,b include features 115 adapted to receive a tool for assembly of the third set of pistons 130a,b into the second set of pistons 120a,b and the second plugs 114a,b into the open ends 113aii,bii of the fifth channels 113a,b.

A sealed channel end 120ai of the first portion 121a of the first piston 120a of the second set of pistons 120a,b forms a wall of a first channel 140a of a second set of sealed channels 140a,b. A sealed channel end 120bi of the first portion 121b of the second piston 120b of the second set of pistons 120a,b forms a wall of a second channel 140b of the second set of sealed channels 140a,b. The sealed channel ends 120ai,bi of the first portions 121a,b of the second set of pistons 120a,b are the opposite ends of the first portions 121a,b to spring ends 120aii,bii of the first portions 121a,b which are adapted to contact the springs 125a,b. The sealed channel ends 120ai,bi of the second set of pistons 120a,b are the rearmost faces of the second set of pistons 120a,b. The second set of sealed channels 140a,b include holes 141 through the mounting body 52. The second set of sealed channels 140a,b include a port 142 which connects the holes 141 to tubes 181b which are connected to a second valve 182b. The second set of sealed channels 140a,b are in fluid communication with the second valve 182b which is in fluid communication with the pressurized air source 184 through a tube 183b. When the second valve 182b is actuated to open, the second set of sealed channels 140a,b is pressurized and a pressure differential is created between the sealed channel ends 120ai,bi of the second set of pistons 120a,b and other axially facing faces of the second set of pistons 120a,b. The pressure differential forces the second set of pistons 120a,b frontwards until the third set of pistons 130a,b contacts a frontward end 126ai,bi of the third channel slot 126a,b. When the second valve closes and no longer pressurizes the second set of sealed channels 140a,b, the springs 125a,b force the second set of pistons 120a,b back to an original position, with the third set of pistons 130a,b contacting a rearward end 126aii,bii of the third channel slot 126a,b. The third set of pistons 130a,b are fixed to the second set of pistons 120a,b and the third set of pistons 130a,b cannot move frontward and rearward relative to the block 111. Therefore, the sampler 1 is adapted to automatically move the block 111 frontward and backward through pneumatically actuating the second set of pistons 120a,b.

The sealed channel ends 130ai of the third portion 134a of the first piston 130a of the third set of pistons 130a,b forms a wall of a first channel 150a of a third set of sealed channels 150a,b. The sealed channel end 130bi of the third portion 134b of the second piston 130b of the third set of pistons 130b forms a wall of a second channel 150b of the third set of sealed channels 150a,b. The sealed channel ends 130ai,bi of the third set of pistons 130a,b are the lowermost faces of the third set of pistons 130a,b. The third set of sealed channels 150a,b include holes through the block 111. The third set of sealed channels 150a,b include a port 152 which connects the holes 151 to tubes 181c which are connected to a third valve 182c. The third set of sealed channels 150a,b are in fluid communication with the third valve 182c which is connect to the pressurized air source 184 with a tube 183c. When the third valve 182c is actuated, the third set of sealed channels 150a,b are pressurized and a pressure differential is created between the sealed channel ends 130ai,bi of the third set of pistons 130a,b and other axially facing faces of the third set of pistons 130a,b. The pressure differential forces the third set of pistons 130a,b upwards relative to the block 111 until the second portion 133a,b of the third set of pistons 130a,b contacts the top faces 113ai,bi of the fifth channels 113a,b. Since the third set of pistons 130a,b is vertically fixed, the third set of pistons 130a,b moving upwards relative to the block is the block 111 moving downwards. When the third valve 182c closes and no longer pressurizes the third set of sealed channels 150a,b, the springs 135a,b force the block 111 upwards.

However, the movement of the block 111 is also governed by bearings 160a,b running through bearing channels 161a,b. The bearing channels 161a,b are channels in bearing channel blocks 162a,b. The bearing channel blocks 162a,b are mounted with bolts onto the main body 70. The bearing channel blocks 162a,b include a first bearing channel block 162a with a first bearing channel 161a on the first side 2a of the sampler 1. The bearing channel blocks 162a,b include a second bearing channel block 162b with a second bearing channel 161b on the second side 2b of the sampler 1. The bearing channels 161a,b run frontward, rearward, upward and downward. The bearing channels 161a,b are substantially in the shape of the letter "U". The bearings 160a,b include a shaft 163a,b fixed to the block 111. Outer rotating members 164a,b of the bearings 160a,b are adapted to contact side walls 165a,b of the bearing channels 161a,b. The side walls 165a,b all face upwards, downwards, frontwards and/or backwards. The width of the bearing channels 161a,b are substantially the same as an outer diameter of the outer rotating members 164a,b. Substantially being within 10%. Therefore, movement of the bearings 160a,b perpendicular to longitudinal lines 166a,b along the bearing channels 161a,b at the location of the bearings 160a,b is minimized. The bearing channels 161a,b include curved corners 167a,b adapted to guide the bearings 160a,b around corners of the bearing channels 161a,b. At least two portions of the side walls 165a,b of the bearing channels 161a,b are adapted to contact and/or be at a distance within 5% of a diameter of the bearings 160a,b to the bearings 160a,b when the bearings 160a,b are at any location in the bearing channels 161a,b. The bearings 160a,b are adapted to roll along the side walls 165a,b of the bearing channels 161a,b.

The block 111 is adapted to be automatically moveable to the dispensing position and a flushing position. The block 111 is shown in the dispensing position in FIGS. 1-13. The flushing position is where the flushing ports 31a,b are coaxial and covering the needles 23a,b. The block 111 is moved from the dispensing position to the flushing position with the following steps. The third valve 182c is opened allowing pressurized air into the third set of sealed channels

150a,b. The pressurized air forces the block 111 downwards. As the block 111 moves downwards, the bearings 160a,b move down first vertical channels 161ai,bi of the bearing channels 161a,b until the bearings 160a,b contact horizontal channels 161aii,bii of the bearing channels 161a,b. The second valve 182b is then opened allowing pressurized air into the second set of sealed channels 140a,b. The pressurized air forces the second set of pistons 120a,b and therefore the block 111 forwards. As the block 111 moves forwards, the bearings 160a,b move forward along the horizontal channels 161aii,bii of the bearing channels 161a,b until the bearings 160a,b contact second vertical channels 161aiii,biii of the bearing channels 161a,b. In this position the block 111 is in a lowermost and forward most position. The block 111 is adapted such that the sample containers 40 can be inserted in the two holes 111a,b of the block 111 in this position. The first, second and third valves 182a-c are all adapted to release pressurized air from the tubes 181a-c and the first, second and third set of sealed channels 100a-b, 140a-b, 150a-b, respectively, when the first, second, third and fourth valves 182a-d are closed or do not allow pressurized air from the pressurized air source 184 into each of the tubes 181a-d. The third valve 182c is then closed and releases pressurized air in the third set of sealed channels 150a,b. The block 111 is then forced upwards by the springs 135a,b until the bearings 160a,b contact tops of the second vertical channels 161aiii,biii. The block 111 is then in the flushing position.

The block 111 is adapted to be automatically moveable from the flushing position to the dispensing position with a reverse of the operations above to move the block 111 from the dispensing position to the flushing position and includes the following steps:

The third valve 182c is opened allowing pressurized air into the third set of sealed channels 150a,b.

The pressurized air forces the block 111 downwards.

As the block 111 moves downwards, the bearings 160a,b move down the second vertical channels 161aiii,biii until the bearings contact the horizontal channels 161aii,bii of the bearing channels 161a,b.

The second valve 182b is then closed and releases pressurized air in the second set of sealed channels 140a,b and the springs 125a,b force the block 111 rearwards.

As the block 111 moves rearwards, the bearings 160a,b move rearward along the horizontal channels 161aii,bii until the bearings 160a,b contact the first vertical channels 161ai,bi.

The third valve 182c is then closed and releases pressurized air in the third set of sealed channels 150a,b and the springs 135a,b force the block 111 upwards until the bearings 160a,b contact tops of the first vertical channels 161ai,bi. The block 111 is then in the dispensing position.

The automatic movement of the block 111 described above is controlled by a controller 190. The controller 190 is adapted to actuate solenoids in the first, second, third and fourth valves 182a-d to open and/or close the first, second, third and fourth valves 182a-d. The controller 190 is adapted to control the first, second, third and fourth valves 182a-d through a wire 196. The controller 190 may be adapted to actuate the valves 182a-d in the sample dispenser 1 in response to input from a user.

The block 111 further includes a cooling device 200. The cooling device 200 is adapted to circulate a cooling fluid between the pipe of the sample fluid vessel and the block 111. The fluid may be water, a refrigerant, sample fluid or other another fluid. Preferably, the fluid is water. The cooling fluid may be circulated between a first sealed cavity in contact with the pipe of the sample fluid vessel and a second sealed cavity 201 in contact with the block 111. The cooling fluid may be circulated through tubes 202. The cooling fluid may be passively circulated between the first and second sealed cavities through diffusion. The cooling fluid may be actively circulated between the first and second cavities with a pump.

Preferably, the sampler 1 is adapted such that the needles 23a,b are covered during transportation of the sampler 1 and/or the sample fluid vessel. Preferably, the sampler 1 is adapted such that the block 111 is in the flushing position with the needles 23a,b covered by the flushing ports 31a,b during transportation of the sampler 1 and/or sample fluid vessel. The flushing ports 31a,b include a flushing channel 32. The flushing channel 32 connects to both flushing ports 31a,b. The flushing channel 32 includes a flushing channel port 33 which is adapted to connect to a flushing channel tube 181d. The flushing channel tube 181d is connected to a fourth valve 182d. The fourth valve 182d is connected to a shuttle valve 170 with a tube 183d. The shuttle valve 170 is adapted to receive a cleaning substance 175 through a first shuttle valve tube 171 and pressurized air through a second shuttle valve tube 172. An end 172a of the first shuttle valve tube 171 is adapted to be located at a base 173a of a pressurized bottle 173. A bottle pressure tube 174 is adapted to be connected to the pressurized bottle 173 and the pressurized air source 184 to pressurize the pressurized bottle 173. The pressurized bottle 173 is adapted to be filled with the cleaning substance 175. The cleaning substance 175 may be any chemical solution adapted to clean surfaces. Preferably, the cleaning substance 175 is a mixture of alcohol and water. Most preferably, the mixture of alcohol and water includes 50%-70% alcohol and 50-25% water. Most preferably, the water is distilled water. Preferably, the shuttle valve 170 is adapted such that when the fourth valve 182d is open alcohol from the pressurized bottle 173 and/or pressurized air from the pressurized air source passes through the shuttle valve 170, through the fourth valve 182d, through the flushing channel 32, through the flushing ports 31a,b, through and around the needles 23a,b, through the outlet 20, through the flexible tubes 60a,b, through the inlet 10a,b, out the outer ends 12a,b of the inlet pipes 11a,b and into the sample fluid vessel. The shuttle valve 170 may be actuated to selectively release pressurized air and/or cleaning substance 175 through the shuttle valve 170. The shuttle valve may be actuated manually or automatically with the controller 190. The flushing device 30 includes the shuttle valve 170, pressurized bottle 173, pressurized air source 184 and tubes 181d, 183d, 172, 171, 174 between the components of the flushing device 30. Therefore, the flushing device 30 is adapted to flush pressurised flushing fluid past all surfaces of the sampler 1 which contact the sample fluid. The flushing fluid being the cleaning substance 175 and pressurized air.

The first, second, third and fourth valves 182a-d may be manually and/or automatically actuated to open or close. Preferably, the first, second, third and fourth valves 182a-d are automatically actuated to open or close. Preferably, the first, second, third and fourth valves 182a-d include solenoids adapted to actuate the first, second, third and fourth valves 182a-d. Preferably, the solenoids are controlled by the controller 190. The controller 190 may include at least one of the following: CPU (central processing unit), relay, switch, buttons, touch screen, display and a communications module. The communications module may be adapted to connect to the internet through WiFi and/or a cellular network. The controller 190 may be controlled with or sent information to an application on a user's personal electronic device or through a website. The controller 190 may be powered by a road vehicle which the sample fluid vessel is mounted to. The controller 190 may include other power sources such as solar and battery.

The controller 190 further includes a pressure sensor, sample fluid temperature sensor and ambient temperature sensor. The pressure sensor and sample fluid temperature sensors are mountable to an inner surface of the cavity of the sample fluid vessel. The pressure sensor is mounted vertically level with or below the first and second inlet pipes 11$a,b$. The ambient temperature sensor is located inside the controller 190. The pressure sensor communicates with the controller 190 through a first wire 191. The sample fluid temperature sensor communicates with the controller 190 through a second wire 192. The first and second wires 191, 192 may each include multiple wires. The controller 190 logs sample fluid temperature from the sample fluid temperature sensor, ambient temperature around the sampler 1 from the ambient temperature sensor and pressure of the sample fluid in the sample fluid vessel at the height of the pressure sensor. The controller uses the sample fluid temperature, ambient temperature and pressure to adjust the revolutions of the motor 64 of the peristaltic pump 61 for the dispensing process to maintain the same amount of sample fluid dispensed in the dispensing process within for example +−1 millilitre. The effects of each of the sample fluid temperature, ambient temperature and pressure on the amount of sample fluid dispensed with a number of revolutions of the motor 64 on the amount of sample fluid dispensed in a dispensing process are preprogramed into the controller 190 and/or adjusted incrementally during use of the sampler 1. The controller 190 uses the pre-programmed effects and sample fluid temperature, ambient temperature and pressure at the time of dispensing to calculate the required revolutions of the motor 64 to result in a desired amount of sample fluid dispensed in the dispensing process. The controller 190 then rotates the motor 64 for the required revolutions during the dispensing process.

The controller 190 is adapted to send/receive information from/to a website and/or application on the user's electronic mobile device. The controller 190 is adapted such that the user can view data from the controller 190 and/or send controls to the controller to, for example, start the dispensing and/or flushing process. The controller 190 is adapted to record the global location and time where/when a dispensing process took place.

The sample containers 40 include RFID (radio frequency identification) tags 193$a,b$ which communicate with RFID devices 194$a,b$ in each of the holes 111$a,b$ of the sample holders 110. The RFID devices 194$a,b$ are adapted to read and write to the RFID tags 193$a,b$. The RFID devices write to the RFID tags on each of the sample containers 40 the time and location that the dispensing process took place when those sample containers 40 were in the sample holders 110. Therefore, advantageously, when the sample fluid in each of the sample containers 40 is tested, the person testing with be able to read the RFID tag on the sample container 40 to identify the time and location the sample fluid was dispensed into the sample container 40. The RFID devices 194$a,b$ are adapted to communicate with the controller 190 through a wire 195.

Unless otherwise stated, references of components with like numbers but are distinguished by the letters "a" and "b" such as reference numbers 120$a$ and 120$b$ refer to the component with a reference with the letter "a" being on the first side 2$a$ of the sampler 1 and the component with a reference with the letter "b" being on the second side 2$b$ of the sampler 1. The components including the tubes 181$a$-$d$, 183$a$-$d$, 174, 172, 171, 202, valves 182$a$-$d$, air pressure source 184, pressurized bottle 173 and the controller 190 shown in FIG. 1 are schematic drawings and may not represent the location, length and shape of the components.

Definitions

Throughout the specification and claims the word "comprise" and its derivatives are intended to have an inclusive rather than exclusive meaning unless the contrary is expressly stated or the context requires otherwise. That is, the word "comprise" and its derivatives will be taken to indicate the inclusion of not only the listed components, steps or features that it directly references, but also other components, steps or features not specifically listed, unless the contrary is expressly stated or the context requires otherwise.

In the present specification, object terms such as "apparatus", "means", "device" and "member", or similar terms, may refer to singular or plural items and are terms intended to refer to a set of properties, functions or characteristics performed by one or more items or components having one or more parts. It is envisaged that where the object term is described as being a unitary object, then a functionally equivalent object having multiple components is considered to fall within the scope of the object term, and similarly, where the object term is described as having multiple components, a functionally equivalent but unitary object is also considered to fall within the scope of the object term, unless the contrary is expressly stated or the context requires otherwise. In the present specification, the phrase "and/or" refers to severally or any combination of the features. For example, the phrase "feature 1, feature 2 and/or feature 3" includes within its scope any one of the following combinations: Feature 1 or feature 2 or feature 3; feature 1 and feature 2 or feature 3; feature 1 or feature 2 and feature 3; feature 1 and feature 2 and feature 3. In this specification, unless otherwise stated, the term "substantially" refers to above 80% by weight.

Where the word "for" is used to qualify a use or application of an object term, the word "for" is only limiting in the sense that the device or component should be "suitable for" that use or application.

Orientational terms used in the specification and claims such as vertical, horizontal, top, bottom, upper and lower are to be interpreted as relational and are based on the premise that the component, item, article, apparatus, device or instrument will usually be considered in a particular orientation, typically with the sample holder the lowermost.

In the present specification, a "pipe" may include a rigid or flexible pipe, or a flexible or bendable hose or tube.

The term "integral" means formed of one body in a single process. In particular, the term "integrally formed" means formed of the one body without post-forming attachment of separately formed component parts. That is, "integrally formed" and the similar term "unitarily formed" mean formed in a single forming process and do not include post-forming attachment of component parts by means of fastener or other component fixing substances or methods.

The invention claimed is:

1. A sampler including an inlet, an outlet, a sample dispenser and a flushing device, the sampler adapted to receive a sample fluid through the inlet, and to dispense the sample fluid through the outlet into sample containers, wherein:
  the flushing device is adapted to;
    flush a pressurized flushing fluid past all contact surfaces of the sample dispenser which are adapted to contact the sample fluid; and
    on actuation to:
      move a flexible conveyance from a compressed state to a non-compressed state; and
      deliver a pressurised flushing fluid passed all of the contact surfaces.

2. The sampler as claimed in claim 1, wherein the flexible conveyance includes at least one flexible tube, the contact surfaces are the internal wall surfaces of the flexible tube, the flexible conveyance forming part of a peristaltic pump that is adapted to pump sample fluid from the inlet, out the outlet and into the sample containers.

3. The sampler as claimed in claim 1, wherein the outlet includes a needle and the flushing device includes a flushing port moveable into and out of alignment with the needle.

4. The sampler as claimed in claim 3, wherein the sampler includes a sample holder including a block adapted to hold the sample containers and the block is adapted to be moveable from a flushing position to a dispensing position and to reversably move from the dispensing position to the flushing position.

5. The sampler as claimed in claim 4, wherein when the block is in a dispensing position, the needle is coaxial with a hole in the block, the flushing port is adapted to receive the needle, the block is moveable to selectively align with the hole of the block and the block is moveable along two axes.

6. The sampler as claimed in claim 4, wherein the sample dispenser further includes a controller and sensors, the controller adapted to adjust a number of revolutions of an output shaft of the pump in the dispensing process based on measurements from the sensors, the sensors include a sample fluid temperature sensor, an ambient temperature sensor and a pressure sensor, the measurements from the sensors including temperature of sample fluid inside the sample fluid vessel from the sample fluid temperature sensor, ambient temperature around the sampler from the ambient temperature sensor and pressure of the sample fluid in the sample fluid vessel at a location vertically level or lower than the inlet from the pressure sensor.

7. The sampler as claimed in claim 4, wherein the sampler includes a sample holder adapted to support the sample containers.

8. The sampler as claimed in claim 7, wherein the sampler includes a cooling device adapted to cool at least one portion of the sample holder the sampler is adapted to be mounted on a pipe of the sample fluid vessel, and the cooling device is adapted to circulate a cooling fluid between the pipe of the sample fluid vessel and the block.

9. The sampler as claimed in claim 1, wherein the sampler is adapted such that the sample fluid which flows through the inlet is taken from an actively flowing stream of sample fluid from or in the sample fluid vessel.

10. The sampler as claimed in claim 1, wherein a flushing process includes the flushing device flushing the pressurized flushing fluid past all surfaces of the sampler which are adapted to contact the sample fluid.

11. The sampler as claimed in claim 10, wherein the sample dispenser is adapted such that the sample holder is moveable from a dispensing position where the sample containers are under the outlet and a flushing position where flushing ports are under the outlet, the sample dispenser adapted to carry out the dispensing process when the sample holder is in the dispensing position and the flushing process when the sample holder is in the flushing position.

12. The sampler as claimed in claim 1, wherein the pressurized flushing fluid is a mixture of air, alcohol and water.

13. The sampler as claimed in claim 2, wherein the peristaltic pump includes a flexible tube and a rotating member engaged with the output shaft of the pump and with peripheral surfaces adapted to contact a first side of the flexible tube.

14. The sampler as claimed in claim 13, wherein the sample dispenser includes a clamp adapted to removably contact a second side of the flexible tube and compress the flexible tube between the clamp and the peripheral surfaces of the rotating member.

15. The sampler as claimed in claim 14, wherein the clamp is locked in contact with the flexible tube and released with in part a pneumatically operated piston.

16. The sampler as claimed in claim 13, wherein the flexible tube is mountable to and spans between barbed pipes of the inlet and outlet, the barbed pipes each including only a single circumferential barb.

* * * * *